United States Patent [19]

Chapdelaine et al.

[11] Patent Number: 5,656,626

[45] Date of Patent: *Aug. 12, 1997

[54] SUBSTITUTED NITROGEN HETEROCYCLES

[75] Inventors: Marc Jerome Chapdelaine, Wilmington; Timothy W. Davenport; Laura E. Garcia-Davenport, both of New Castle, all of Del.; Paul Francis Jackson, Chadds Ford, Pa.; Jeffrey A. McKinney, West Chester, Pa.; Charles D. McLaren, Landenberg, Pa.

[73] Assignee: Zeneca Limited, London, United Kingdom

[*] Notice: The term of this patent shall not extend beyond the expiration date of Pat. No. 5,502,048.

[21] Appl. No.: 547,696

[22] Filed: Oct. 19, 1995

Related U.S. Application Data

[63] Continuation of Ser. No. 255,613, Jun. 9, 1994, Pat. No. 5,502,048.

[30] Foreign Application Priority Data

Jun. 10, 1993 [GB] United Kingdom ............... 9311948

[51] Int. Cl.$^6$ ......................... A61K 31/55; C07D 223/16
[52] U.S. Cl. ............................................. 514/213; 540/523
[58] Field of Search ............................. 514/213; 540/523

[56] References Cited

U.S. PATENT DOCUMENTS

| | | | |
|---|---|---|---|
| 4,410,520 | 10/1983 | Watthey | 424/244 |
| 4,473,575 | 9/1984 | Watthey | 424/263 |
| 4,477,446 | 10/1984 | Jones | 424/260 |
| 4,575,503 | 3/1986 | Watthey | 514/213 |
| 4,885,364 | 12/1989 | Thottathil | 540/523 |
| 5,051,442 | 9/1991 | Salituro et al. | 514/419 |
| 5,182,366 | 1/1993 | Huebner et al. | 530/334 |
| 5,189,054 | 2/1993 | Salituro et al. | 514/483 |
| 5,229,413 | 7/1993 | Gray et al. | 514/509 |
| 5,266,684 | 11/1993 | Rutter et al. | 530/334 |
| 5,322,776 | 6/1994 | Knopf et al. | 435/304 |
| 5,322,943 | 6/1994 | McCall et al. | 544/360 |
| 5,330,768 | 7/1994 | Park et al. | 424/501 |
| 5,492,905 | 2/1996 | Harris et al. | 514/213 |
| 5,502,048 | 3/1996 | Chapdelaine et al. | 514/213 |

FOREIGN PATENT DOCUMENTS

| | | |
|---|---|---|
| 91037158 | 5/1990 | Canada. |
| 0072352 | 2/1983 | European Pat. Off.. |
| 0130538A | 1/1985 | European Pat. Off.. |
| 0396124 | 5/1990 | European Pat. Off.. |
| 0400665 | 6/1990 | European Pat. Off.. |
| 0459561A2 | 5/1991 | European Pat. Off.. |
| 0481676A1 | 10/1991 | European Pat. Off.. |
| 0483881A1 | 11/1991 | European Pat. Off.. |
| 0489458A1 | 11/1991 | European Pat. Off.. |
| 0542689A1 | 11/1992 | European Pat. Off.. |
| 0555042A1 | 2/1993 | European Pat. Off.. |
| 0610553A1 | 10/1993 | European Pat. Off.. |
| 3416695 | 11/1985 | Germany. |
| 3034977A | 1/1991 | Japan. |
| 1340334 | 12/1973 | United Kingdom. |
| 2103614 | 2/1983 | United Kingdom. |
| 2265372 | 9/1993 | United Kingdom. |
| 9105-549 | 5/1991 | WIPO. |
| 91/16307 | 10/1991 | WIPO. |
| 92/11854 | 7/1992 | WIPO. |
| 92/13535 | 8/1992 | WIPO. |
| 94/00124 | 1/1994 | WIPO. |
| 94/07500 | 4/1994 | WIPO. |
| 94/15598 | 7/1994 | WIPO. |
| 94/18990 | 9/1994 | WIPO. |
| 94/18989 | 9/1994 | WIPO. |

OTHER PUBLICATIONS

J. Org. Chem., 40, 3874 (1975).
Can. J. Chem., 52, 610, (1974).
J. Heterocyclic Chem., 26, 793, (1989).
Molecular Pharmacology, 41:1130–1141 (1992).
Kokoko Pat. No. Sho. 49–28754 (1974) (translation provided) (JP).
Kokoko Pat. No. Sho. 49–28753 (1974) (translation provided) (JP).
Abstract of EP–166–353–A (Jan. 2, 1986) no date.
Abstract of EP–166–357–A (Jan. 2, 1986) no date.
Abstract of EP–166–354–A (Jan. 2, 1986) no date.
Abstract of US 4,692,522 (Sep. 8, 1987) no date.
Abstract of US 4,757,068 (Jul. 12, 1988) no date.
Abstract of EP–322–779–A (Jul. 5, 1989) no date.
Abstract of ZA 8303–903–A (Oct. 1, 1984) no date.
Abstract of EP–107–095–A (May 2, 1984) no date.
Abstract of ZA 8309–532–A (Jun. 24, 1985) no date.
Abstract of US 3,989,689 (Nov. 2, 1976) no date.
Abstract of Jap. 4028–754 (Jul. 29, 1974) no date.
Abstract of US 4,477,446 (Oct. 16, 1984) no date.
Abstract of US 3,949,081 (Apr. 6, 1976) no date.
Abstract of US 4,965,356 (Oct. 27, 1990) no date.
Abstract of EP 400–665–A (Dec. 5, 1990) no date.
Chemical Abstracts, 82, 1975, 614.
J. Med. Chem. 1990, 33, 2944–2946.
J. Med. Chem. 1994, 37, 1402–1405.
J. Med. Chem. 1990, 33, 3130–3132.
J. Med. Chem. 1992, 35, 3423–3425.
Abstract, 206th ACS Mtg. Chicago, 1993, MEDI 183 no date.
Abstract #B–73, 33rd National Organic Chemistry Symposium no date.
The Pharmacologist, vol. 35–#3, 1993.
Neuroscience Research Communications, vol. 8, #3, 1991.
International Search Report Oct. 13, 1994.

*Primary Examiner*—Robert T. Bond
*Attorney, Agent, or Firm*—Michael D. Alexander

[57] ABSTRACT

Antagonists at the NMDA receptor complex which are benz[b]azepines having a hydroxy, alkoxy or amino substituent at the 3-position and a 4-position alkenyl, alkynyl, aryl or heteroaryl substituent for treatment of stroke and/or other neurodegenerative disorders.

11 Claims, No Drawings

SUBSTITUTED NITROGEN HETEROCYCLES

This application is a continuation of our prior application Ser. No. 08/255,613, filed Jun. 9, 1994, now U.S. Pat. No. 5,502,048.

This invention relates to substituted nitrogen hererocycles, in particular to substituted benz[b]azepine compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, psychosis, Huntington's chorea, amyotrophic lateral sclerosis, Alzheimer's disease, Parkinson's disease, Olivo-pontocerebellar atrophy, vital-induced neurodegeneration such as in acquired immunodeficiency syndrome and its associated dementia, anoxia such as from drowning, spinal cord and brain trauma, poisoning by exogenous neurotoxins, and chronic pain, for the prevention of drug and alcohol withdrawal symptoms, and for the inhibition of tolerance and dependence to opiate analgesics. The invention particularly relates to novel substituted benz[b]azepine compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

The compounds provided by this invention may be useful in a variety of neurodegenerative disorders because they function as excitatory amino acid antagonists. They may do so indirectly, via allosteric modulation of the glutamate binding site, specifically by acting as antagonists of the strychnine-insensitive glycine receptor on the NMDA receptor complex. They may also do so directly, by binding to the glutamate site itself on the NMDA receptor complex.

3-Amino-4-methyl-2,5-dioxo-2,5-dihydro-1H-benz[b]azepine is disclosed in J. Org. Chem., 40, (1975), 3874–3877. Kokoku Patent No. Sho. 49-28754, published 29 Jul. 1974, refers to certain benz[b]azepines which bear an amino group or a dialkyl-substituted aminoalkylamino group, or a 3-substituent referred to as a "cyclic amino group composed of a 5- or 6-membered ring". Benz[b]azepines which bear a hydroxy or alkoxy group at the 3-position and which are unsubstituted at the the 4-position are referred to in published PCT patent application no. WO 92/11854; UK 1,340,334; Can. 3. Chem., 52(4), 610–615; Mol. Pharmacol., 41(6), 1130–41; and J. Het. Chem., 26, (1989), 793.

According to the invention there is provided a Compound of the invention which is a compound of formula I (formula set out, together with other formulae referred to by Roman Numerals, on pages following the Examples), wherein R denotes 0–3 substituents on the benz-ring selected independently from halo, trifluoromethyl and cyano;

$R^3$ is hydroxy, (1–6C)alkyloxy (which may bear a carboxy or (1–3C)alkoxycarbonyl substituent) or $NR^aR^b$ in which $R^a$ and $R^b$ are independently selected from hydrogen, (1–6C)alkyl, (2–6C)alkenyl, (3–7C)cycloalkyl, (3–7C)cycloalkyl(1–6C)alkyl, aryl, aryl(1–6C)alkyl, heteroaryl, heteroaryl(1–6C)alkyl and $CH_2Y$ in which Y is (CHOH)$_n$CH$_2$OH or $(CH_2)_nR^c$ (wherein n is an integer from 1 to 5) and in which $R^a$ and $R_b$ (except when $CH_2Y$) independently may bear a $COR^c$ substituent; or $NR^aR^b$ forms a pyrrolyl, pyrrolinyl, pyrrolidinyl, piperidino, piperazinyl, morpholino, thiomorpholino (or S-oxide) or perhydroazepinyl ring which may further bear one or more (1–6C)alkyl, phenyl, phenyl(1–4C)alkyl, phenoxy or phenyl(1–4C)alkyl substituents;

$R^4$ is (2–6C)alkenyl, (2–6C)alkynyl, aryl or heteroaryl and $R^4$ independently may bear $COR^c$; —OH or —O(1–4C)alkyl; (1–4C)alkyl, -(1–4C)alkylcarboxy(1–4C)alkyl, aryl or —Si— and wherein $R^c$ is hydroxy, (1–4C)alkoxy, or $NR^dR^e$ in which $R^d$ and $R^e$ are independently selected from hydrogen,(1–3C)alkyl, benzyl or phenyl wherein the aryl portion may be unsubstituted or substituted with halogen, (1–4C)alkyl or (1–5C)O— or other typical aromatic sustituents; or $NR^dR^e$ forms a pyrrolyl, pyrrolinyl, pyrrolidinyl, piperidino, piperazinyl (which may bear a (1–3C)alkyl or benzyl substituent at the 4-position), morpholino, thiomorpholino (or S-oxide) or perhydroazepinyl ring;

and in which an aryl or heteroaryl portion of $R^3$ or $R^4$ may bear one or more halo, trifluoromethyl, (1–6C)alkyl, (2–6C)alkenyl, phenyl, phenyl(1–4C)alkyl, hydroxy, (1–6C)alkoxy, phenoxy, phenyl(1–4C)alkoxy, nitro, amino, (1–4C)acylamino, trifluoroacetylamino, carboxy, (1–3C)alkoxycarbonyl or a phenyl carbonyl group; a 1,3 dioxolo group; a -(1–4C)alkylNRR' wherein R or R' is H or (1–4C)alkyl; a -(1–4C)alkylCN or cyano substituents;

or a pharmaceutically acceptable salt thereof.

According to the invention there is further provided a Compound of the invention which is a compound of formula I (formula set out, together with other formulae referred to by Roman Numerals, on pages following the Examples), wherein R denotes 0–3 substituents on the benz-ring selected independently from halo, trifluoromethyl and cyano;

$R^3$ is hydroxy, (1–6C)alkyloxy (which may bear a carboxy or (1–3C)alkoxycarbonyl substituent) or $NR^aR^b$ in which $R^a$ and $R^b$ are independently selected from hydrogen, (1–6C)alkyl, (2–6C)alkenyl, (3–7C)cycloalkyl, (3–7C)cycloalkyl(1–6C)alkyl, aryl, aryl(1–6C)alkyl, heteroaryl, heteroaryl(1–6C)alkyl and $CH_2Y$ in which Y is (CHOH)$_n$CH$_2$OH or (CH—) $R^c$ (wherein n is an integer from 1 to 5) and in which $R^a$ and $R_b$ (except when $CH_2Y$) independently may bear a $COR^c$ substituent; or $NR^aR^b$ forms a pyrrolyl, pyrrolinyl, pyrrolidinyl, piperidino, piperazinyl, morpholino, thiomorpholino (or S-oxide) or perhydroazepinyl ring which may further bear one or more (1–6C)alkyl, phenyl, phenyl(1–4C)alkyl, phenoxy or phenyl(1–4C)alkyl substituents;

$R^4$ is (2–6C)alkenyl, (2–6C)alkynyl, aryl or heteroaryl and $R^4$ independently may bear a $COR^c$ substituent; and wherein $R^c$ is hydroxy, (1–3C)alkoxy, or $NR^dR^e$ in which $R^d$ and $R^e$ are independently selected from hydrogen and (1–3C) alkyl or $NR^dR^e$ forms a pyrrolyl, pyrrolinyl, pyrrolidinyl, piperidino, piperazinyl (which may bear a (1–3C)alkyl or benzyl substituent at the 4-position), morpholino, thiomorpholino (or S-oxide) or perhydroazepinyl ring;

and in which an aryl or heteroaryl portion of $R^3$ or $R^4$ may bear one or more halo, trifluoromethyl, (1–6C)alkyl, (2–6C)alkenyl, phenyl, phenyl(1–4C)alkyl, hydroxy, (1–6C) alkoxy, phenoxy, phenyl(1–4C)alkoxy, nitro, amino, (1–4C) acylamino, trifluoroacetylamino, carboxy, (1–3C)alkoxycarbonyl or cyano substituents;

or a pharmaceutically acceptable salt thereof.

The invention further provides a pharmaceutical composition for the treatment of neurological disorders comprising a compound of formula I as defined above, or a pharmaceutically acceptable salt thereof, and a pharmaceutically acceptable diluent or carrier.

Thus, the present invention also provides a compound of formula I (as defined above), or a pharmaceutically acceptable salt thereof, for use in medicine; and in particular the use of a compound of formula I (as defined above) for the manufacture of a medicament for treating neurological disorders.

While not wishing to be bound by theory, it is believed that a Compound of the invention in which $R^3$ is not hydroxy may be active as a drug in their its own right and/or that it may serve as a prodrug and be converted in vivo into the corresponding Compond of the invention is which $R^3$ is hydroxy, the 3-hydroxy derivative being active per se. The 3-methoxy derivatives shown as Examples 3a, 8, 7a, 10, 32, 36, 58 and 63 are useful as intermediates in the syntheses of the corresponding hydroxy derivatives and may also be useful as pro-drugs. In addition, all of the 3-methoxy derivatives of the claimed compounds are useful as intermediates in the production of the corresponding hydroxy compounds as well as pro-drugs.

It will be appreciated that the compounds of formula I may contain one or more asymmetically substituted carbon atoms such that such compounds may be isolated in optically active, racemic and/or diastereomeric forms. Some compounds may exhibit polymorphism. It is to be understood that the present invention encompasses any racemic, optically-active, diastereomeric, polymorphic or stereoisomeric form, or mixtures thereof, which form possesses excitatory amino acid antagonist properties, it being yell known in the art how to prepare optically-active forms (for example, by resolution of the racemic form or by synthesis from optically-active starting materials) and how to determine the excitatory amino acid antagonist properties by the standard tests described hereinafter. It may be preferred to use the compound of formula I in a form which is characterized as containing, for example, at least 95%, 98% or 99% enantiomeric excess of a particular form.

In this specification R, $R^3$, $R^a$ et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five ring atoms consisting of carbon and one to four heteroatonms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof.

A pharmaceutically acceptable salt is one made with an acid or base which provides a physiologically acceptable counterion. In addition, the present invention relates to crystalline, amorphous or polymorphs of the compounds of formula I and those claimed and exemplified herein.

Particular values are listed below for radicals, substituents and ranges for illustration only and they do not exclude other defined values or other values within defined ranges for the radicals and substituents. A particular value for R is for example chloro or bromo; for $R^3$ is hydroxy, methoxy, ethoxy or amino; and for $R^4$ is vinyl, allyl, alkynyl, phenyl, furyl, thienyl, thiophenyl or pyridyl and suitable salt forms thereof such as HBr salts in which $R^4$ may bear a substituent chosen from —OH, —O(1–4C)alkyl, -(1–4C)alkylcarboxy (1–4C)alkyl, phenyl, trimethylsilyl or may bear a $COR^e$ substituent selected from carboxy, methoxycarbonyl, ethoxycarbonyl, t-butyloxycarbonyl, carbamoyl, N-methylcarbamoyl, N-phenylcarbamoyl, N-p-ethoxyphenylcarbamoyl, N-methylphenylcarbamoyl, N-diflourophenylcarbamoyl or N-isopropylphenylcarbamoyl, and N,N-dimethylcarbamoyl or N,N-methylphenylcarbamoyl. When R4 is phenyl it may bear a substituent selected from hydroxy, methoxy, benzoyl, Di(C1–4)alkylamino(1–4C)alkyl, 1,3 dioxolo, cyano (1–6C) alkyl, nitro, phenoxy, methoxycarbonyl and ethoxycarbonyl. The heteroaryl group may be further substituted with (1–4C) alkoxy and a alkylene carbon on the heteraryl ring may be substituted with —B(OH)O— wherein the radical oxygen bonds to the 3 position of the benz[b]azepine ring system to form a six-membered boronic ring. When $R^4$ is a vinyl group substituted with a hydroxy at the 1-carbon, the enol species is equivalent to a methyl or alkyl ketone with the carbonyl directly attached to the 4-position of the benz[b]azepine ring. The 1-alkoxy substituted vinyl derivative is a useful intermediate in producing the alkylcarbonyl compounds of the present invention. R4 may be substituted at any carbon with the substituents described previously. For example, if R4 is vinyl, the substituent may be at the 1-vinyl or 2-vinyl carbon. In addition, for example, the 2-vinyl carbon may be disubstituted. In the vinylation reactions, the trans olefin is the predominant isomer produced. The present invention, however, also includes the minor cis isomers. One particular group of compounds is one in which the benz-ring is unsubstitued or bears two substituents R at the 6- and 8-positions or bears one substituen R at the 8-position and R, $R^3$ and $R^4$ have any of the definitions described above; a more particular subgroup is one in which the benz-ring bears one substituent R at the 8-position, especially an 8-chloro substituent. Another particular group of compounds is one in which $R^3$ is hydroxy, methoxy or ethoxy and R and $R^4$ have any of the definitions described above.

Compounds of the invention which are of particular interest include the compounds described in the accompanying Examples, and their pharmaceutically acceptable salts, and are hence provided as a further feature of the present invention.

The benz[b]azepines of the present invention can be made by processes which may include processes known in the chemical arts for the production of structurally analogous compounds. Such processes for the manufacture of novel benz[b]azepines as defined above are provided as further features of the invention and are illustrated by the following procedures in which the meanings of generic radicals are as given above unless otherwise qualified. Thus, according to the present invention there is also provided a process for the preparation of a novel benz[b]azepines of formula I, which process is selected from:

(a) For a compound of formula I in which $R^3$ is alkoxy and R4 is vinyl, alkynyl, aryl, heteroaryl or substituted versions thereof, reacting a corresponding compound of formula II in which $R^1$ is alkoxy and $R^2$ is bromo or iodo with a tin reagent of formula $R^4SnL_3$ in which L is a suitable ligand. A suitable value for L includes, for example, (1–6C) alkyl, with butyl being preferred. It may be preferred to use a reagent of formula , $(R^4)_4Sn$. A preferred value for $R^2$ is iodo. Suitable catalysts include palladium catalysts conveniently introduced as palladium(II) species, such as for example trans-benzyl(chloro)bis(triphenylphosphine) palladium(II) or bischlorobistriphenyl phosphine palladium (Pd II), or as palladium(O) species, such as for example the catalyst prepared from tri(2-furyl)phosphine or triorthotolylphosphine and tris(dibenzylideneacetone)dipalladium (O). Generally, the reaction is carried out in an inert hydrocarbon solvent such as toluene at a temperature from about ambient temperature to the reflux temperature of the reaction mixture, preferably at the reflux temperature of the reaction mixture. DMF is an alternative solvent when the bischlorobis (Pd II) catalyst is used. In some cases, as shown in the Examples, an amine such as triethylamine may be added to the coupling reaction. The 4-alkenoic acid derivatives are readily prepared by deesterfying the corresponding alkoxy carbonyl species in a suitable solvent such as $CH_2Cl_2$ and with an acid such as $CF_3COOH$. Likewise, the corresponding 3-hydroxy species may be readily prepared by hydrolysis of the 3-methoxy alkenoic acid derivative using, for example, aqueous sodium bicarbonate or other suitable base. Furthermore, under circumstances wherein the target compound is a 3-hydroxy-4-alkoxycarbonylalkenyl species, the precursor 3-methoxy species is treated with, for example, a solution of lithium hydroxide monohydrate in THF or other suitable solvent.

The 4-alkenoic acid compounds are also utilized to prepare the carbamoyl species (acrylamides) of the present invention. For example, aniline or other suitable amine or substituted amine ($NR^1R^2$) wherein $R^1$ and $R^2$ is H, alkyl or aryl may be added to a 3-alkoxy, 4-alkenoic acid in DMF or other suitable solvent using N-methyl morpholine or other known HCl scavenger to form the claimed carbamoyl compounds. The corresponding 3-hydroxy species may be formed by reacting the 3-alkoxy species with lithium hydroxide monohydrate or other suitable base in water or by treatment with $BBr_3$ followed by aqueous sodium bicarbonate. The alkyloxycarbonyl alkenyl (e.g. propenyl) compounds of the present invention are readily prepared from the 3-alkoxy 4-iodo compounds and the appropriate acrylate or substituted acrylate using a palladium catalyst as described herein. A 4-alkoxy carbonyl alkenyl series as shown herein may be selectively hydrolyzed to either the 3-hydroxy, 4 [n-carboxy] alkenyl series or the 3-alkoxy, 4-[n-carboxy] alkenyl series. In some circumstances, the resulting acrylate species may cyclize to form a lactone (or lactam if 3-$NH_2$) if there is a 3-hydroxy group on the benz[b]azepine ring.

This process is generally preferred to that described in (b) below when there is a substituent R.

(b) For a compound of formula I in which $R^3$ is alkoxy and $R^4$ is alkenyl or alkynyl in which the double or triple bond is not adjacent to the benz[b]azepine ring, reacting a corresponding compound of formula II in which $R^1$ is alkoxy and $R^2$ is hydrogen with a compound of formula $R^4Z$, in which Z is a suitable leaving group, in the presence of a strong base. A suitable value for Z includes, for example, halo such as bromo or iodo, methanesulfonyloxy, trifluoromethanesulfonyloxy and p-toluenesulfonyloxy. A suitable strong base includes, for example, an alkyl lithium compound such as butyl lithium. Generally, the reaction will be carried out in an inert solvent such as tetrahydrofuran in the presence of two equivalents of the strong base (or a slight excess over two equivalents) and in the presence of an amine such as diisopropylamine. An alkalai metal salt such as lithium chloride also may be present, and the reaction conveniently may be carried out at a temperature of about $-78°$ to $-20°$ C., thereby forming a dianion, followed by reacting the dianion thereby prepared with the compound of formula $R^4Z$ (for example $R^4I$) at a temperature of about $-40°$ to about $25°$ C.

(c) For a compound of formula I in which $R^3$ is hydroxy, cleaving the alkoxy group of a corresponding compound of formula I in which $R^3$ is alkoxy. Generally, the cleavage is carried out using a compound in which $R^3$ is methoxy and using a boron trihalide, preferably boron tribromide, in an inert solvent such as dichloromethane at ambient temperature.

(d) For a compound of formula I in which $R^3$ is $NR^aR^b$ reacting a corresponding compound of formula I in which $R^3$ is alkoxy with an amine of formula $HNR^aR^b$. Generally, the reaction is carried out using a compound of formula I in which $R^3$ is methoxy. The reaction may be carried out using an excess of the amine as a solvent or by using a polar solvent such as a lower alcohol or dimethyl formamide, at a range of 0 ° C. to about 150° C., preferably using a pressure vessel for a lower boiling amine.

(e) For a compound of formula I in which $R^3$ is pyrrolyl, reacting a corresponding compound of formula I in which $R^3$ is amino with a 2,5-dialkoxytetrahydrofuran, particularly 2,5-dimethoxytetrahydrofuran. Generally, the reaction is carried out in a solvent such as glacial acetic acid and at a temperature from about ambient temperature to reflux temperature.

It may be desired to optionally use a protecting group during all or portions of the above described processes; the protecting group then may be removed when the final compound is to be formed.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. Such reactions and modifications include, for example, introduction of nitro or halogeno, reductive alkylation of nitro. The reagents and reaction conditions for such procedures are well known in the chemical art.

Pharmaceutically acceptable salts may be formed with some compounds of the present invention using standard procedures well known in the art, for example by reacting a sufficiently basic compound of formula I with a suitable acid affording a physiologically acceptable anion, or by reacting a sufficiently acidic compound of formula I with a suitable base affording a physiologically acceptable cation, or by any other conventional procedure.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures or the procedures described in the Examples.

A starting material of formula II in which $R^1$ is alkoxy and $R^2$ is bromo or iodo conveniently may be prepared by halogenating a corresponding compound of formula II in which $R^2$ is hydrogen. Suitable halogenating reagents include for example bromine and iodine monochloride.

A starting material of formula II in which $R^1$ is alkoxy and $R^2$ is hydrogen conveniently may be obtained by using a published procedure, for example as described in one of the references listed above as disclosing benz[b]azepines which bear a hydroxy or alkoxy group at the 3-position and which are unsubstituted at the 4-position.

In general, a compound of formula II in which $R^1$ is alkoxy and $R^2$ is hydrogen is obtained by reacting a corresponding alkyl enol ether of formula III in which $R^1$ is alkoxy with sodium azide in neat trifluoromethanesulfonic acid or concentrated sulfuric acid (Schmidt reaction) at a temperature of about 0° C. to about room temperature. Trifluoromethanesulfonic acid is preferred in cases where any one or more substituents R is present and is halogen. $R^1$ is preferably methoxy or ethoxy to facilitate the Schmidt reaction.

A methyl enol ether of formula III may be made by reacting a corresponding hydroxy naphthoquinone of formula III in which $R^1$ is hydroxy with a corresponding alcohol, such as methanol or ethanol, in the presence of a suitable acid such as anhydrous hydrogen chloride. A hydroxy naphthoquinone of formula III in which $R^1$ is hydroxy may be made by oxidizing a corresponding tetralone of formula IV or of formula V. The oxidation conveniently can be effected as a one-pot process in a suitable solvent such as tert-butanol and in the presence of a suitable base such as potassium tert-butoxide, with oxygen bubbled through the rection mixture. In a preferred process the tetralone of formula IV may be oxidized to the corresponding hydroxy naphthoquinone of formula III in which $R^1$ is hydroxy by bubbling oxygen through a solution of potassium bis(trimethylsilyl)amide in dimethylformamide, adding the tetralone and continuing to bubble oxygen through the reaction mixture until the oxidation is complete. This process is described in the alternative procedure described in the second part of Example 1.c. It will also be appreciated by those skilled in the art that suitable stepwise or multi-pot variations of the one-pot process can be implemented.

Many tetralones of formula IV and/or V suitable for use in the invention are either available commercially or can be made by procedures already known in the art. It is noted that many enol ethers of formula III can also be made along the lines generally disclosed in S. T. Petri at. al., Org. Syn., 69, 220 and in J. M. Heerding and H. W. Moore, J. Org. Chem., 56, 4048–4050, (1991). The synthesis is generally discussed and illustrated in Scheme I in the published PCT patent application no. W0 92/11854 listed above.

When used to intervene therapeutically following a stroke, a benz[b]azepine of the present invention is generally administered as an appropriate pharmaceutical composition which comprises a benz[b]azepine of the present invention (as defined hereinbefore) together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; and in the form of sterile solutions or suspensions for administration by intravenous or intramuscular injection or infusion.

The dose of compound of the present invention which is administered will necessarily be varied according to principles well known in the art taking account of the route of administration, the severity of the ischemic disorder, and the size and age of the patient. In general, e compound of formula I will be administered to a warm blooded animal (such as man) so that an effective dose is received, for example an intravenous dose in the range of about 0.1 to about 10 mg/kg body weight.

It will be apparent to those skilled in the art that a compound of the present invention can be co-administered with other therapeutic or prophylactic agents and/or medicaments that are not medically incompatible therewith.

As mentioned previously, the compounds of the present invention (and their pharmaceutically acceptable salts) are useful in treating neurological disorders in mammals such as man.

The actions of compounds of formula I as antagonists at the glycine receptor of the NMDA receptor complex can be shorn by standard tests such as the [$^3$H]-glycine binding assay, by functional assays in vitro such as tests for measuring glutamate evoked contractions of the guinea pig ileum, and by tests in vivo such as ischemia induced by carotid occlusion in the gerbil model. The beneficial pharmacological properties of the compounds of the present invention may be demonstrated using one or more of these techniques.

Test A. [$^3$H]-(glycine Binding Assay. In the [$^3$H]-glycine binding assay, neuronal synaptic membranes are prepared from adult (about 250 g) male Sprague-Dawley rats. Freshly dissected cortices and hippocampi are homogenized in 0.32M sucrose (110 mg/mL). Synaptosomes are isolated by centrifugation (1000×g, 10 min), the supernatant is pelleted (20,000×g, 20 min) and resuspended in double-distilled water. The suspension was centrifuged for 20 minutes at 8,000×g. The resulting supernatant and buffy coat are washed twice (48,000×g, 10 mins, resuspension in double-deionized water). The final pellet is quickly frozen (dry ice\ethanol bath) under double-deionized water and stored at −70° C.

On the day of the experiment, thawed synaptic membranes are homogenized with a Brinkmann Polytron (tm, Brinkmann Instruments, Westbury, N.Y.) tissue homogenizer in 50 mM tris(hydroxymethyl)aminomethane citrate, pH 7.1. The membranes are incubated with 0.04% Sufact-AMPS X100 (tm, Pierce, Rockford, Ill.) in buffer for 20 minutes at 37° C. and washed six times by centrifugation (48,000×g, 10 min) and resuspended in buffer. The final pellet is homogenized at 200 mg wet weight/mL of the buffer for the binding assay.

For [$^3$H]-glycine binding at the N-methyl-D-aspartate receptor, 20 nM [$^3$H]-glycine (40–60 Ci/mmol, New England Nuclear, Boston, Mass.) is incubated with the membranes suspended in 50 mM tris (hydroxymethyl) aminomethane titrate, pH 7.1 for 30 minutes at 4° C. Glycine, 1 mM, is used to define the nonspecific binding. Bound [$^3$H]-glycine is isolated from free using a Brandel (Biomedical Research and Development Laboratories, Gaithersburg, Md.) cell harvester for vacuum filtration over glass fiber filters (Whatman GF/B from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. $IC_{50}$ values are obtained from a least-squares regression of a logit-log transformation of the data.

For glutamate evoked contractions of the guinea pig ileum, the methodology is as described previously (Luzzi at. al., Br. J. Pharmacol., 95, 1271–1277 (1989). The longitudinal muscle and associated myenteric plexus are removed and placed in oxygenated modified Krebs-Henseleit solution (118 mM NaCl, 4.7 mM KCl, 2.5 mM $CaCl_2$, 1.2 mM $KH_2PO_4$, 25 mM $NaHCO_3$, and 11 mM glucose). Tissues are suspended on glass rods in organ baths under a resting tension of 0.5 g. After an initial depolarization with 80 mM potassium to remove possible blockade of the NMDA receptor channel complex with magnesium, twitch responses are evoked with 100 µM glutamate. Isometric mechanical responses are recorded. Tissues are equilibrated for at least 2 hours prior to addition of compounds.

A dose response curve for the effect of the unknown on the magnitude of the glutamate-evoked contractions is generated. Glutamate-evoked contractions are generated at 20 minute intervals, with the test compound added 5 minutes before the glutamate. The magnitude of the contraction with each dose of the unknown is expressed relative to the control, the third contraction evoked by 100 µM glutamate alone in the same tissue bath. The $IC_{50}$ is obtained from a least-squares regression of a logit-log transformation of the data.

After the last contraction for the dose-response curve, 100 µM glycine is added to the bath 10 minutes after the previous addition of glutamate. 10 minutes later the estimated $IC_{50}$ to $IC_{70}$ dose of the test compound is added and 10 minutes later glutamate is used to evoke the contraction. The "glycine reversal" is the ability of glycine to compete with the unknown and to prevent the inhibition previously seen by the dose of the unknown.

Test B. Gerbil Ischemic Model. When testing in vivo using the gerbil ischemic model, adult female Mongolian gerbils (50–70 g) are anesthetized with 2 to 3% halothane. The bilateral common carotid arteries at the neck are exposed and occluded with microaneurysm clips. After 10 min (unless specified), the clips are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped. Gross behavioral observations along with motor activity are recorded for 2 hours on the first (24 hour) day following the occlusion. After 4 days, subjects are sacrificed (decapitation), brains are removed, fixed, sectioned and stained with hematoxylin/eosin and cresyl violet.

The brain sections are rated for neuronal damage in the hippocampus using the following rating scale:

0=undamaged, normal

1=slight damage (up to 25%)—restricted CA1/subiculum border

2=moderate damage (up to 50%)—obvious damage, restricted to less than half of CA1 field 3=marked damage (up to 75%)—involving greater than half of CA1 field 4=damage extending beyond CA1 field Results can be reported as the percentage of neuroprotection afforded by a particular dose and dosing regimen.

Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxcon-Rank Sum test.

In general, the action of a Compound of the invention as an antagonist at the glycine receptor of the NMDA receptor complex can be be shown in Test A with an $IC_{50}$ of 100 µM or much less and/or in Test B in which a statistically significant level of neuroprotection (relative to sham-operated control) is found when the Compound is dosed twice intraperitoneally (ip) at 20 mg/kg of body weight according to the above protocol. The compounds of the present invention, unless exemplified as an intermediate only, are useful as glycine receptor antagonists and, for example, have IC50s of less than or much less than 100 micromolar.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; coupling constants (J) are given in Hz;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported.

EXAMPLE 1

8-Chloro-3-methoxy-2,5-dioxo-4-vinyl-2,5-dihydro-1H-benz[b]azepine

8-Chloro-4-iodo-3-methoxy-2,5-dioxo-2,5-dihydro-1H-benz[b]azepine (0.21 g) was suspended in toluene (5 mL)

and trans-benzyl(chloro)bis(triphenylphosphine)palladium (II) (45 mg) was added, followed by tributylvinyltin (0.23 mL). The resulting mixture was stirred at reflux for 17 hours, cooled to room temperature, poured into saturated aqueous ethylenediaminetetraacetic acid (10 mL), and extracted with tetrahydrofuran:ether (1:1). The combined extracts were dried and evaporated to yield a yellow powder. Chromatography, with chloroform as the eluent, yielded the title compound as a white powder (80 mg); mp 212°–214° C. (dec); NMR: 11.44 (s,1), 7.55 (m,1), 7.30 (m,2), 6.69 (dd,1, J=17.7, 11.6), 5.90 (dd,1, J=17.7, 1.8), 5.52 (dd,1, J=11.5, 1.8), 3.8 (s,3). Analysis for $C_{13}H_{10}ClNO_3 \cdot 0.2\ H_2O$; Calculated: C, 58.42; H, 3.92; N, 5.24: Found: C, 58.48; H, 3.87; N, 5.06.

The starting iodide was prepared as follows.

a. 4-(4-Chlorophenyl)butyric acid. 3-(4-Chlorobenzoyl)propionic acid (49.94 g) was dissolved in triethylene glycol (320 mL). To the stirred solution was added potassium hydroxide (44.5 g) followed by 98% hydrazine hydrate (29.0 g). The mixture was heated to reflux (142° C.) for 2 hours. Water and hydrazine hydrate were distilled at atmospheric pressure; the pot temperature rose to 195°–200° C. After 0.5 hour at 195°–200° C., the mixture was cooled to ambient temperature and diluted with water (320 mL). The aqueous solution was poured into 6N hydrochloric acid (200 mL) and further diluted with 200 mL of ice water. Upon standing, a solid formed which was filtered, washed (water) and dried under vacuum (25° C., 15 Pa) to afford the acid as a white solid (43.61 g).

b. 7-Chloro-1-tetralone. 4-(4-Chlorophenyl)butyric acid (26.62 g) was added to 150 g of hot polyphosphoric acid (90° C.); the mixture was maintained at 90°–95° C. for 0.33 hour. After cooling to room temperature, the reaction mixture was added to 400 mL of ice-cold stirred water. The solution was allowed to warm to room temperature; and the resulting precipitate was filtered, washed (water) and air dried to give a pale yellow solid (22.3 g). The solid was recrystallized from toluene (50 mL) at −10° C. The crystals were collected and washed with cold toluene and then hexanes to give the tetralone as pale yellow crystals (18.18 g); mp 100.3°–101.1° C.

c. 7-Chloro-2-hydroxy-1,4-naphthoquinone. 7-Chloro-1-tetralone (27.56 g) was dissolved in 445 mL dry tert-butanol and added over a one hour period to a solution of freshly sublimed potassium tert-butoxide (102.7 g) in tert-butanol (1.15 L) saturated with oxygen. Oxygen was bubbled through the solution for two hours after completion of the addition. The mixture was poured into stirred ice cold 2N hydrochloric acid (1.9 L) and extracted with diethyl ether. The ethereal extracts were evaporated to give a yellow solid, which was triturated with ethyl acetate. The solid was filtered, washed (water) and dried under vacuum (25° C., 15 Pa). A portion of the yellow solid (10.5 g) was then taken up in hot ethyl acetate (0.5 L) and the solution was concentrated to 50 mL. Crystallization was initiated by cooling the solution in an ice bath. The solid was filtered, washed (cold ethyl acetate and hexane) and dried under vacuum (25° C., 15 Pa), to give yellow plates (7.10 g); mp 215°–216.5° C.

Alternatively, the intermediate 7-chloro-2-hydroxy-1,4-naphthoquinone can be prepared from 7-chloro-1-tetralone using the following procedure.

A 1-liter 4-neck flask, equipped with thermometer, medium frit gas diffusion inlet tube with in-line antisuckback trap, 250 mL addition funnel, and magnetic stirring, was charged with dry dimethylformamide (75 mL) and 0.5M potassium bis(trimethylsilyl)amide (KHMDS) in toluene (222 mL, 111 mmol). The stirred pale yellow solution was cooled to 5° C., the introduction of gaseous oxygen was begun at a rate of 70 to 100 mL/minute, and 7-chloro-1-tetralone (10 g) dissolved in dry dimethylformamide (125 mL) was added dropwise at a rate such that the reaction temperature was held below 15° C. with the aid of external ice bath cooling. The addition required about 30 minutes. Oxygen addition was continued until the starting material was consumed (about 1.5 hour) as determined by TLC (eluent 3:1 chloroform:methanol); samples for TLC spotting were prepared by acidifying several drops of reaction mixture to about pH 1 with 2N hydrochloric acid and extracting with ethyl acetate. During the reaction period the mixture gradually became bright red in color, and red solid began to separate out. At the end of the reaction period, the mixture was checked for the presence of peroxides using enzyme (peroxidase) catalyzed, redox indicator test paper. The mixture was quenched with ice cold 4N hydrochloric acid (250 mL), and the resulting yellow mixture was stirred for 30 minutes. The bright yellow product was filtered and the filter cake washed with ether and dried to afford the naphthoquinone (5.47 g). The filtrate was placed in a separatory funnel; and the organic layer was separated, dried and evaporated. The residue was triturated with ether. Additional product separated and was filtered and dried (1.14 g).

d. 7-Chloro-2-methoxy-1,4-naphthoquinone. 7-Chloro-2-hydroxy-1,4-naphthoquinone (0.73 g) was added to 4% (w/w) hydrogen chloride in methanol (14 mL). The solution was heated to reflux for 0.5 hour. Upon cooling to room temperature, a precipitate formed which was filtered, washed (methanol) and dried under vacuum (25° C., 15 Pa) to give an orange solid (0.72 g); 250 MHz NMR: 8.10 (d,1, J=2.2), 8.04 (d,1, J=8.3), 7.71 (dd,1, J=8.3, 2.2), 6.19 (s,1), 3.92 (s,3).

e. 8-Chloro-3-methoxy-2,5-dioxo-2,5-dihydro-1H-benz[b]azepine. 7-Chloro-2-methoxy-1,4-naphthoquinone (0.71 g) was added to concentrated sulfuric acid (4.1 mL) chilled in an ice bath. The cold red solution was stirred under nitrogen, and sodium azide (0.23 g) was added. The reaction mixture was maintained in an ice bath for 0.33 hour and was then allowed to warm to room temperature for 18 hours. The reaction mixture was cooled in an ice bath, and an additional portion of sodium azide (0.21 g) was added. After 0.33 hour the mixture was allowed to warm to room temperature for 20 hours. The mixture was cooled in an ice bath, and sodium azide (0.21 g) was added; the mixture was maintained in an ice bath for 0.33 hour and then at room temperature for 68 hours. The reaction mixture was then poured into ice cold saturated aqueous sodium bicarbonate (200 mL). The resulting precipitate was filtered, washed (water) and dried under vacuum (25° C., 15 Pa) to give a dark solid. The solid was recystallized from dimethylformamide (3 mL) and water (1 mL) to give the benz[b]azepine as a white solid (0.2 g); 250 MHz NMR: 11.39 (s,1, NH), 7.93 (d,1, J=8.8), 7.47 (d,1, J=1.7), 7.28 (dd,1, J=8.8, 1.7) 6.35 (s,1), 3.80 (s,3).

Alternatively, the 8-chloro-3-methoxy-2,5-dioxo-2,5-dihydro-1H-benz[b]azepine can be prepared from 7-chloro-2-methoxy-1,4-naphthoquinone using the following procedure.

7-Chloro-2-methoxy-1,4-naphthoquinone (14.74 g) was added to trifluoromethanesulfonic acid (153 mL) chilled in an ice bath, and sodium azide (4.74 g) was added. The reaction mixture was maintained in an ice bath for 0.33 hour then allowed to warm to room temperature and maintained thus for 90 hours. The reaction mixture was recooled in an ice bath, and an additional portion of sodium azide (2.15 g)

was added. After 0.08 hour the mixture was allowed to warm to room temperature for 19 hours. The reaction mixture was then poured into ice cold aqueous sodium bicarbonate (2.3 L). The resulting precipitate was filtered, washed (water) and dried under vacuum (25° C., 15 Pa) to give a tan solid (13.83 g). The solid was recrystallized from hot dimethylformamide (300 mL) and dried under vacuum (25° C., 15 Pa) to give the benz[b]azepine as a light tan solid (8.12 g); mp 340°–342° C. (dec). Analysis for $C_{11}H_8ClNO_3$: Calculated: C, 55.60; H, 3.39; N, 5.89; Found: C, 55.35; H, 3.38; N, 6.07.

f. 8-Chloro-4-iodo-3-methoxy-2,5-dioxo-2,5-dihydro-1H-benz[b]azepine. To a suspension of 8-chloro-3-methoxy-2,5-dioxo-2,5-dihydro-1H-benz[b]azepine (3.00 g) in glacial acetic acid (250 mL) was added sodium acetate (2.07 g) followed by iodine monochloride (15.2 mL). The mixture was heated to reflux for 1.5 hours, was allowed to cool, and the acetic acid was evaporated from the reaction mixture. The solid residue was suspended in tetrahydrofuran and stirred for 15 minutes. The solution was filtered and the resulting filtrate evaporated. The yellowish solid was recrystallized from refluxing toluene (700 mL) to afford the 4-iodo compound (3.8 g); 250 MHz NMR: 11.60 (broad s, 1), 7.59 (d,1, J=7.1), 7.30 (d,1, J=1.4), 7.23 (dd,1, J=7.1, 1.6), 3.90 (s,3). Analysis for $C_{11}H_7ClINO_3$: Calculated: C, 36.34; Z, 1.94; N, 3.85; Found: C, 36.35, H, 1.87; N, 3.82.

EXAMPLE 2

4-Allyl-8-chloro-3-methoxy-2,5-dioxo-2,5-dihydro-1H-benz[b]azepine

A solution of tri(2-furyl)phosphine (0.019 g) and tris(dibenzylideneacetone)dipalladium(O) (0.020 g) in toluene (25 mL) was allowed to stir for 10 minutes. To this solution was added 8-chloro-4-iodo-3-methoxy-2,5-dioxo-2,5-dihydro-1H-benz[b]azepine (0.750 g), followed by allyltributyltin (0.83 g). The reaction mixture was heated to reflux for 16 hours, was allowed to cool, and the toluene was evaporated. The residue was dissolved in ethyl acetate, and the resulting solution was filtered through silica gel and stirred over an equal volume of 1 molar aqueous potassium fluoride for 0.5 hour. The organic portion was separated, washed (water, brine), dried, filtered through diatomaceous earth and evaporated. The resulting orange solid was triturated with hexanes and subsequently chromatographed, with ethyl acetate:hexanes (5:1) as the eluent, to afford the title compound (0.189 g); mp 135°–136° C.; NMR: 11.43 (broad s,1), 7.63 (d,1, J=8.5), 7.36 (d,1, J=2.0), 7.29 (dd,1, J=8.6, 1.9), 5.85–5.72 (m,1), 5.00–4.96 (m,1), 4.94 (m,1), 3.80 (s,3), 3.28 (m,2). Analysis for $C_{14}H_{12}ClNO_3$ 0.25 $H_2O$.: Calculated: C, 59.58; H, 4.46; N, 4.96; N, 4.96; Found C, 59.74; H, 4.39; N, 4.93.

EXAMPLE 3

4-Allyl-8-chloro-3-hydroxy-2,5-dioxo-2,5-dihydro-1H-benz[b]azepine

To a solution of 4-allyl-8-chloro-3-methoxy-2,5-dioxo-2,5-dihydro-1H-benz[b]azepine (0.159 g) in dichloromethane (10 mL) was added boron tribromide (1M in dichloromethane, 1.8 mL). After 1.5 hours, the reaction mixture was quenched with 50 mL of saturated aqueous sodium bicarbonate. Dichloromethane (30 mL) was added and the mixture was adjusted to pH 3 using 2.4N hydrochloric acid. The organic portion was separated, washed (water, brine), dried and evaporated. The resulting yellowish solid was triturated with hexanes to afford the title compound (0.074 g); mp 172°–174° C.; NHR: 11.73 (s,1), 10.39 (s,1), 7.93 (d,1, J=8.6), 7.48 (s,1), 7.30 (dd,1, J=8.8, 2.1), 5.86–5.73 (m,1), 5.01–4.91 (m,2), 3.35 (m,2). Analysis for $C_{13}H_{10}ClNO_3$.0.25 $H_2O$: Calculated: C, 58.22; H, 3.95; N, 5.22; Found: C, 58.18; H, 3.91; N, 5.13.

EXAMPLE 3a

4-Allyl-8-chloro-3-methoxy-2,5-dioxo-2,5-dihydro-1H-benz[b]azepine

The title compound was prepared in a procedure similar to that described in Example 4 below except the 8-chloro species rather than the deschloro species was utilized.

EXAMPLE 4

4-Allyl-3-methoxy-2,5-dioxo-2,5-dihydro-1H-benz[b]azepine

A solution of 3-methoxy-2,5-dioxo-2,5-dihydro-1H-benz[b]-azepine (10 g), lithium chloride (12.5 g) and diisopropylamine (7.5 mL) in tetrahydrofuran (200 mL) was cooled to −70° C.; and butyllithium (2.5M in hexanes, 43 mL) was added, maintaining the temperature below −60° C. The mixture was warmed to 20° C. for 1 hour, and cooled to −70° C. A portion of the resulting 2,5-dihydro-2,5-dioxo-1,4-dilithio-3-methoxy-1H-benz[b]azepine solution (0.188M in tetrahydrofuran, 26 mL) was added to a solution of allyl bromide (0.85 mL) in tetrahydrofuran (15 mL) at −70° C. The mixture was warmed to room temperature, diluted with water, acidified (2N hydrochloric acid) and extracted with ethyl acetate. The combined organic extracts were washed with brine, dried and evaporated. The solid was purified by chromatography, with ethyl acetate:toluene (1:3) as the eluent, to give the title compound (0.189 g, 34%); NMR: 5.77 (m,1); 4.99 (d,1) 4.94 (s,1) 3.29 (d,2); MS: m/z=244 (M+1).

EXAMPLE 5

4-Allyl-3-hydroxy-2,5-dioxo-2,5-dihydro-1H-benz[b]azepine

To a solution of 4-allyl-3-methoxy-2,5-dioxo-2,5-dihydro-1H-benz[b]azepine (0.2 g) in dichloromethane was added boron tribromide (1M in dichloromethane, 3 mL). The precipitate that formed was diluted with water and extracted with ethyl acetate. The combined organic extracts were washed with brine, dried and evaporated using toluene to azeotrope the water. The solid was recrystallized from hot toluene to give the title compound (0.14 g); mp 174°–175 ° C.; NMR: 5.80 (m,1); 5.03 (s,1); 4.98 (d,1); 3.38 (d,2); MS: m/z=229(M+1). Analysis for $C_{13}H_{11}NO_3$.0.1 $H_2O$: Calculated: C, 67.58; H, 4.89; N, 6.06; Found: C, 67.63; H, 4.88; N, 5.95.

EXAMPLE 6

8-Chloro-3-methoxy-4-(4-nitrophenyl)-2,5-dioxo-2,5-dihydro-1H-benz[b]azepine

8-Chloro-4-iodo-3-methoxy-2,5-dioxo-2,5-dihydro-1H-benz[b]azepine (0.50 g) was dissolved in toluene (12 mL). To this stirred suspension was added trans-benzyl(chloro)bis(triphenylphosphine)palladium(II) (0.050 g) and tributyl (4-nitrophenyl)tin (0.70 g). The resulting suspension was stirred at reflux for 48 hours, then cooled to room temperature, applied directly to a silica column (1.5 cm by 15 cm), and eluted with dichloromethane (250 mL), (ether:dichloromethane (20:80)(250 mL), and methanol:dichloromethane (5:95)(250 mL) to afford the title product (0.30 g, 61%) as a light green solid; mp 250°–251° C. (dec); NMR: 8.24 (d,2, J=9.0), 7.68 (d,1, J=8.6), 7.54 (d,2, J=8.9), 7.42 (d,1, J=2.0), 7.32 (dd,1, J=9.0, 2.1), 3.72 (s,3); MS: m/z=359(M+1).

The tin reagent for the above reaction was prepared as follows.

a. Tributyl(4-nitrophenyl)tin. 1-Iodo-4-nitrobenzene (2.5 g) was dissolved in toluene (100 mL). To this was added trans-benzyl(chloro)bis(triphenylphosphine)palladium (II) (0.1g) and bis(tributyltin) (6.9 g). The resulting mixture was stirred at 55° C. for 48 hours. The reaction mixture was then added to ether (100 mL) and 10% (w/w) aqueous KF (100 mL). The organic layer was dried, evaporated, and purified by chromatography, eluting with tetrahydrofuran/hexane (2:98), to afford the stannane (1.4 g, 34%) as a clear, light yellow oil; NMR: 8.13 (d,2, J=8.5), 7.13 (d,2, J=8.6), 1.53 (m,6), 1.31 (m,6), 1.12 (m,6), 0.888 (t,9, J=7.2); MS: Cluster matched theoretical molecular ion distribution. In addition, the homo-coupled byproduct 4,4'-dinitrobiphenyl (0.85 g) was isolated.

EXAMPLE 7

8-Chloro-3-hydroxy-4-(4-nitrophenyl)-2,5-dioxo-2,5-dihydro-1H-benz[b]azepine

8-Chloro-3-methoxy-4-(4-nitrophenyl)-2,5-dioxo-2,5-dihydro-1H-benz[b]azepine (125 mg) was dissolved in dichloromethane (10 mL). To this was added boron tribromide (1M in dichloromethane 1 mL). This suspension was stirred for one hour. Saturated sodium bicarbonate (5 mL) was then added, and this mixture stirred for 2–3 minutes. The mixture was then adjusted to pH 3 by addition of 6N HCl. This suspension was stirred for 40 minutes, then vacuum filtered and the collected solid washed with water and crystallized from dimethylformamide (2 mL) and water (6 mL) to yield the title compound (110 mg, 91%) as an off white solid; mp 310°–312° C.; NMR: 11.90 (s,1, NH), 10.7 (broad s,1, OH), 8.26 (dd,2, J=6.9, 2.0), 7.92 (d,1, J=8.7), 7.51 (m,3), 7.34 (dd,1, J=8.7, 2.0); MS: m/z=345(M+1). Analysis for $C_{16}H_9ClN_2O_5$: Calculated: C, 55.75; H, 2.63; N, 8.13; Found: C, 55.49; H, 2.54; N, 8.05

EXAMPLE 7a

8-Chloro-3-methoxy-4-(4-nitrophenyl)-2,5-dioxo-2,5-dihydro-1H-benz[b]azepine

The title compound was prepared in an analogous manner with the previous examples end then utilized as an intermediate to produce Example 7.

EXAMPLES 8, 10, 11, AND 13 ARE SHOWN ON TABLE 2 AND EXAMPLES 9 AND 12 ARE SHOWN ON TABLE 1

Example 8 is named 8-Chloro-3-methoxy-4-phenyl-1H-benzo(b)azepine-2,5-dione

Example 9 is named 8-Chloro-3-hydroxy-4-(3-nitrophenyl)-1H-benzo(b)azepine-2,5-dione Example 10 is named 8-Chloro-3-methoxy-4-(3-nitrophenyl)-1H-benzo(b)azepine-2,5-dione Example 11 is named 8-Chloro-3-methoxy-4-(4-phenoxyphenyl)-1H-benzo(b)azepine-2,5-dione Example 12 is named 8-Chloro-3-hydroxy-4-(4-phenoxyphenyl)-1H-benzo(b)azepine-2,5-dione Example 13 is named 8-Chloro-4-(4-ethoxyphenyl)-3-methoxy-1H-benzo(b)azepine-2,5-dione

EXAMPLE 14

8-Chloro-3-hydroxy-4-phenyl-1H-benzo(b)azepine-2,5-dione

To a solution of 4-Bromo-8-chloro-3-hydroxy-2,5-dioxo-2,5-dihydro-1H-benz[b]azepine (400 mg) in THF (10 mL) was added phenyltrimethylstannane (600 mg) and trans-Benzyl(chloro)bis (triphenyl-phosphinepalladium(II) (50 mg). The solution was heated to reflux for 5 hours at which time a dark gray precipitate formed. The reaction mixture was cooled to room temperature and diluted with an ether-tetrahydrofuran mixture (1:1). This mixture was washed with a 10% solution of potassium fluoride, dried ($Na_2SO_4$), and evaporated to dryness. Chromatography, with ethyl acetate as the eluent, yielded the title compound as a white solid (230 mg); mp 193–196 degrees C.; NMR: 7.18(m,2H), 7.31(m, 4H), 7.52(s, 1H), 7.87(d, 1H, J=8.7), 10.28(brs, 1H), 11.81(s, 1H). Analysis for $C_{16}H_{10}ClNO_3 \cdot 0.3H_2O$: Calculated: C, 62.98, H, 3.50, N, 4.59: Found: C, 62.82, H, 3.33, N, 4.67.

EXAMPLES 17, 21 AND 22 ARE SHOWN ON TABLE 1; EXAMPLES 15 AND 16 ARE SHOWN ON TABLE 3 AND EXAMPLES 18, 20 AND 23 ARE SHOWN ON TABLE 2; EXAMPLE 19 IS SHOWN ON TABLE 4

Example 15 is named 8-Chloro-3-hydroxy-4-(4-methoxyphenyl)-1H-benzo(b)azepine-2,5-dione.

Example 16 is named 8-Chloro-3-hydroxy-4-(3-methoxyphenyl)-1H-benzo(b)azepine-2,5-dione.

Example 17 is named 8-Chloro-3-hydroxy-4-(4-hydroxyphenyl)-1H-benzo(b)azepine-2,5-dione.

Example 18 is named 8-Chloro-4-(4-[(diisopropylamino)methyl]phenyl}-3-methoxy-1H-benzo(b)azepine-2,5-dione.

Example 19 is named 8-Chloro-4-[4-(diisopropylamino)methyl]phenyl}-3-hydroxy-1H-benzo(b)azepine-2,5-dione.

Example 20 is named 4-(4-Benzoylphenyl)-8-chloro-3-methoxy-1H-benzo(b)azepine-2,5-dione.

Example 21 is named 4-(4-Benzoylphenyl)-8-chloro-3-hydroxy-1H-benzo(b)azepine-2,5-dione.

Example 22 is named 4-Benzo[1,3]dioxol-5-yl-8-chloro-3-hydroxy-1H-benzo(b)azepine-2,5-dione.

Example 23 is named [4-(8-Chloro-3-methoxy-2,5-dioxo-2,5-dihydro-1H-benzo(b)azepine-4-yl)phenyl]acetonitrile.

EXAMPLE 24

8-Chloro-3-methoxy-4-(2-thienyl)-1H-benzo(b)azepine-2,5-dione

A solution of tri(2-furyl)phosphine (0.036 g) and tris (dibenzylideneacetonedipalladium (O) (0.26 g) in toluene (50 mL) was allowed to stir for 10 minutes. To this solution was added 8-chloro-4-iodo-3-methoxy-2,5-dioxo-2,5-dihydro-1H- benz[b]azepine (1.0 g), followed by 2-tributylstannylthiophene (1.24 g). The reaction was heated to reflux for 1.5 hours, was allowed to cool, and the toluene was evaporated. The residue was triturated with hot hexanes (75 mL). The title compound was afforded upon filtration (0.76 g); mp >240; NMR: 11.47 (bs, 1), 7.73 (dd, 1, J=5.1, 0.8), 7.60 (d, 1, J=7.9), 7.51 (dd, 1, J=4.0), 7.33 (d, 1, J=7.8), 7.31 (s, 1), 7.14 (dd, 1, J=5.1, 4.1), 3.88 (s, 3). Analysis for $C_{15}H_{10}O_3SClN$: Calculated: C, 56.34; H, 3.15; N, 4.38; Found C, 55.96; H, 3.34; N, 4.33.

EXAMPLE 25

8-Chloro-3-hydroxy-4-(2-thienyl)-1H-benzo(b) azepine-2,5-dione

A solution of 4-(2-thienyl)-8-chloro-3-methoxy-2,5-dioxo-2,5-dihydro-1H-benz[b]azepine (0.20 g) in 2.4N HCl/THF (1:1, 200 mL) was allowed to stir at room temperature for 1 hour followed by heating to 50° C. for 1 hour. The reaction mixture was partitioned between ether and water. The organic portion was dried (MgSO$_4$), filtered, and concentrated in vacuo. The residue was recrystallized twice from ethyl acetate/hexanes to afford the title compound (0.048 g); mp 231°–233° C. (dec.); NMR: 11.70 (bs, 1), 7.72 (d, 1, J=8.6), 7.62–7.60 (m,2), 7.40 (d, 1, J=1.9), 7.32 (dd, 1, J=8.6, 2.0), 7.10 (m, 1). Analysis for C$_{14}$H$_8$O$_3$NClS 0.25 H$_2$O.: Calculated: C, 54.29; H, 2.76; N, 4.51; Found C, 54.38; H, 2.90; N, 4.41.

EXAMPLE 26

9-chloro-4-hydroxybenzo[b]thieno[3',2':3,4][1,2] oxaborinino[5,6-f]azepine-6,12-dione A suspension of 4-(2-thienyl)-8-chloro-3-methoxy-2,5-dioxo-2,5-dihydro-1H-benz[b]azepine (0.67 g) in dichloromethane (250 mL) was treated dropwise with boron tribromide (6.3 mL of a 1 molar solution in CH$_2$Cl$_2$). After stirring at room temperature for 5 minutes, the reaction was quenched by addition of saturated aqueous sodium bicarbonate. The aqueous layer was acidified to pH 1 using 2.4N HCl, and the heterogeneous mixture was allowed to stir for 0.5 hour. The reaction mixture was filtered. The filter cake was triturated with ethyl acetate/ethanol (1:1, 30 mL), affording the title compound (0.38 g); mp >240 C; NMR: 11.63 (bs, 1), 9.95 (bs, 1), 7.94 (bs, 2), 7.66 (bs, 1) 7.49 (bs, 1), 7.32 (d, 1, J=7.5).

EXAMPLE 27

8-Chloro-3-hydroxy-4-thiophen-3-yl-1H-benzo(b) azepine-2,5-dione

A solution of 4-(3-thienyl)-8-chloro-3-methoxy-2,5-dioxo-2,5-dihydro-1H-benz[b]azepine (0.74 g) in 2.4N HCl/THF (1:1, 600 mL) was allowed to stir at room temperature for 48 hours. The reaction mixture was partitioned between ether and water. The organic portion was dried (MgSO$_4$), filtered, and concentrated in vacuo. The residue was recrystallized twice from ethyl acetate/hexanes (2:1) to afford the title compound (0.173 g); mp 248° C. (dec.); NMR: 11.75 (bs, 1), 10.45 (bs, 1), 7.80 (d, 1, J=8.6), 7.64 (m, 1), 7.48 (m, 2), 7.33 (dd, 1, J=8.6, 2.0), 7.15 (dd, 1, J=5.0, 1.2). Analysis for C$_{14}$H$_8$O$_3$NSCl: Calculated: C, 55.00; H, 2.64; N, 4.58; Found C, 54.77; H, 2.81; N, 4.56

EXAMPLE 28

4-(3-thienyl)-8-chloro-3-methoxy-2,5-dioxo-2,5-dihydro-1H-benz[b]azepine

A solution of tri(2-furyl)phosphine (0.046 g) and tris (dibenzylideneacetone)dipalladium (O) (0.046 g) in toluene (75 mL) was allowed to stir for 10 minutes. To this solution was added 8-chloro-4-iodo-3-methoxy-2,5-dioxo-2,5-dihydro-1H-benz[b]-azepine (1.82 g), followed by 3-tributylstannylthiophene (2.2 g). The reaction was heated to reflux for 3 hours. After allowing the reaction mixture to cool to room temperature and stir for 16 hours, a solid precipitated. The filtered solid was recrystallized from ethyl acetate/methanol (2:1) to afford the title compound (0.54 g); NMR: 11.49 (bs, 1), 7.78 (m, 1), 7.63 (d, 1, J=8.4), 7.52 (m, 1), 7.38 (d, 1, J=1.9), 7.30 (dd, 1, J=8.6, 2.1), 7.20 (m, 1), 3.75 (s, 3).

EXAMPLE 29

8-Chloro-4-furan-2-yl-3-methoxy-1H-benzo(b) azepine-2,5-dione

A solution of 4-(2-furyl)-8-chloro-3-methoxy-2,5-dioxo-2,5-dihydro-1H-benz[b]azepine (0.15 g) in 2.4N HCl/THF (1:1, 200 mL) was allowed to stir at room temperature for 8 hours. The reaction mixture was partitioned between ether and water. The organic portion was dried (MgSO$_4$), filtered, and concentrated in vacuo. The residue was recrystallized from ethyl acetate/hexanes (2:1) to afford the title compound (0.06 g); mp 222°–224° C. (dec.); NMR: 11.70 (bs, 1), 10.87 (bs, 1), 7.76–7.72 (m, 2), 7.42 (s, 1), 7.33 (dd, 1, J=8.6, 1.9), 6.79 (m, 1), 6.57 (m, 1). Analysis for C$_{14}$H$_8$O$_4$NCl 0.25 H$_2$O.: Calculated: C, 56.90; H, 2.73; N, 4.74; Found C, 57.31; H, 2.32; N, 4.62.

EXAMPLE 30

8-Chloro-4-furan-2-yl-3-hydroxy-1H-benzo(b) azepine-2,5-dione

A solution of tri(2-furyl)phosphine (0.026 g) and tris (dibenzylideneacetone)dipalladium (O) (0.026 g) in toluene (50 mL) was allowed to stir for 10 minutes. To this solution was added 8-chloro-4-iodo-3-methoxy-2,5-dioxo-2,5-dihydro-1H-benz-[b]azepine (1.0 g), followed by 2-tributylstannylfuran (1.2 g). The reaction was heated to reflux for 0.5 hour, was allowed to cool, and the toluene was evaporated. The residue was triturated with hot hexanes (75 mL). The isolated solid was recrystallized from ethyl acetate/hexanes (1:1) to afford the title compound (0.44 g); mp 233°–234° C.; NMR: 11.47 (bs, 1), 7.79 (s, 1), 7.58 (d, 1, J=8.9), 7.34–7.31 (m, 2), 6.91 (d, 1, J=3.4), 6.61 (m, 1), 3.82 (s, 3). Analysis for C$_{15}$H$_{10}$ClNO$_4$ 0.5 H$_2$O.: Calculated: C, 57.61; H, 3.54; N, 4.47; Found C, 57.77; H, 3.13; N, 4.46.

EXAMPLE 31 IS DESCRIBED IN TABLE 4 AND EXAMPLE 32 IS DESCRIBED IN TABLE 2

Example 31 is named 8-Chloro-3-hydroxy-4-(pyridine-3-carbonyl)-1H-benzo(b)azepine-2,5-dione.

Example 32 is named 8-Chloro-3-methoxy-4-(pyridine-3-carbonyl)-1H-benzo(b)azepine-2,5-dione.

EXAMPLE 33

8-Chloro-3-hydroxy-4-pyridin-2-yl-1H-benzo(b) azepine-2,5-dione

This demethylation is an alternative procedure to that used in example 3. It is the one used for all examples in which the substrate bears a basic nitrogen. This includes examples: 19, 31, 33 and 35.

To a suspension of 8-Chloro-3-methoxy-4-pyridin-2-yl-1H-benzo(b)azepine-2,5-dione (0.390 g) in CH$_2$Cl$_2$ (10 mL) was added 48% HBr (0.45 mL). After 3 hours at 0 degrees C., the mixture was concentrated to dryness. The solid residue was resuspended in tetrahydrofuran (3–4 mL). Trituration and filtration yielded an off-white powder (370 mg=96%). Physical data for the compounds synthesized via this reaction are tabulated in Table 1.

EXAMPLES 34 AND 36 ARE DESCRIBED IN TABLE 2 AND EXAMPLE 35 IS DESCRIBED IN TABLE 4

Example 34 is named 8-Chloro-3-methoxy-4-pyridin-2-yl-1H-benzo(b)azepine-2,5-dione.

Example 35 is named 8-Chloro-3-hydroxy-4-(6-methoxypyridin-2-yl)-1H-benzo[b]azepine-2,5-dione.

Example 36 is named 8-Chloro-3-methoxy-4-(6-methoxypyridin-2-yl)-1H-benzo[b]azepine-2,5-dione.

EXAMPLE 37

4-Acetyl-8-chloro-3-hydroxy-1H-benzo(b)azepine-2,5-dione

To a suspension of 4-(1-ethoxyvinyl)-8-chloro-3-methoxy-2,5-dihydro-1H-benz[b]azepine (330 mg) in $CH_2Cl_2$ at −78 degrees C. was added boron tribromide (6.0 mL). The solution was allowed to warm to 0 degrees C. over a one hour period. To the reaction mixture was then added saturated aqueous sodium bicarbonate (15 mL) followed by 3N HCl (6 mL). This mixture was stirred for 45 minutes and filtered. Crystallization of the crude product from DMF/water yielded a white solid (240 mg); mp 254°–256° C. (decomposes); NMR: 2.32(8, 3H), 7.36(dd, 1H, J1=8.8 Hz, J2=1.9 Hz), 7.49(8, 1H), 8.02(d, 1H, J=8.8 Hz), 11.77(s, 1H). Analysis for $C_{12}H_8ClNO_4$-0.1$H_2O$: Calculated: C, 53.89, H, 3.09, N, 5.24: Found: C, 53.53, H, 2.94, N, 5.34.

EXAMPLE 38 IS DESCRIBED IN TABLE 2

Example 38 is named 8-Chloro-4-(1-ethoxyvinyl)-3-methoxy-1H-benzo(b)azepine-2,5-dione.

EXAMPLE 39

8-Chloro-4-(2-ethoxyvinyl)-3-methoxy-1H-benzo(b)azepine-2,5-dione.

8-Chloro-4-iodo-3-methoxy-2,5-dioxo-2,5-dihydro-1H-benz[b]azepine (5.80 g) was added to a solution of tris-(dibenzylideneacetone)dipalladium (O) (0.10 g) and tri-(2-furyl)phosphine (0.11 g) in toluene (181 mL) at room temperature. The mixture was treated with tri-n-butyl-2-ethoxy-ethenyl stannane (6.18 g; Lensink A. J., Budding H. A., Marsman J. W., *J. Organometal. Chem.* 1967 9 285). The mixture was heated to reflux for 6.5 hours. The mixture was cooled to room temperature and then filtered. The filtrate was concentrated to approximately 50 mL volume as a solid formed. The solid was filtered off, washed with toluene, and air dried to give a light-yellow solid (1.13 g). The solid was dissolved in 11 mL of hot toluene. The solution was cooled to room temperature and the resulting solid was filtered of, washed with cold toluene, washed with hexane, and air dried to give the title compound as a yellow solid.(0.54 g); mp 202.5°–204.1° C.; $^1$H NMR ($d_6$-DMSO) 7.37 (d,1, J=12.6), 5.80 (d,1, J=12.6) for trans olefin protons; MS: m/z=308 (base peak) (M+1). Analysis for $C_{15}H_{14}ClNO_4$: Calculated: C, 58.55; H, 4.59; N, 4.55; Found: C, 58.19; H, 4.46; N, 4.51.

EXAMPLE 40

8-Chloro-3-methoxy-4-phenylethynyl-1H-benzo(b)azepine-2,5-dione

A solution of tri(2-furyl)phosphine (0.019 g) and tris(dibenzylideneacetone)dipalladium (O) (0.02 g) in toluene (25 mL) was allowed to stir for 10 minutes. To this solution was added 8-chloro-4-iodo-3-methoxy-2,5-dihydro-1H-benz[b]azepine (0.75 g) followed by 1-tributylstannyl-2-phenylacetylene (1.7 g). The reaction mixture was heated at 50° C. for 8 hours, was allowed to cool, and the toluene was evaporated. The residue was dissolved in ethyl acetate and stirred over an equal volume of 1 molar aqueous potassium fluoride for 0.5 hour. The organic portion was separated, washed (water, brine), dried (MgSO4), filtered, and concentrated in vacuo. The crude solid was chromatographed over silica gel (ethyl acetate/hexanes 1:1) and subsequently recrystallized from ethyl acetate/hexanes (1:1) to afford the title compound (0.22 g); mp 204°–205° C.; NMR: 11.56 (bs, 1), 7.77 (d, 1, J=8.6), 7.54–7.51 (m, 2), 7.46–7.44 (m, 3), 7.38 (d, 1, J=1.9), 7.33 (dd, 1, J=8.6, 2.0). Analysis for $C_{19}H_{12}O_3NCl$ 0.5 $H_2O$.: Calculated: C, 65.81; H, 3.78; N, 4.04; Found C, 65.45; H, 3.65; N, 4.13. The 3-hydroxy version may readily be prepared according to the procedures described herein.

EXAMPLE 41

8-Chloro-3-methoxy-4-trimethylsilanylethynyl-1H-benzo(b)azepine-2,5-dione

8-Chloro-4-iodo-3-methoxy-2,5-dioxo-2,5-dihydro-1H-benz[b]azepine (6.62 g) was dissolved in 146 mL of DMF at room temperature under argon. The solution was treated with trimethylsilyl acetylene (8.94 g, 12.9 mL) followed by triethylamine (3.68 g, 5.07 mL). The mixture was then treated with bis-chloro-bis-(triphenyl-phosphine) palladium (II) (0.64 g) followed by cuprous iodide (0.51 g). The solution was stirred at room temperature for 3 hours. The mixture was concentrated to a solid. It was treated with cold water and extracted with ethyl acetate. The extract was washed with brine, dried over sodium sulfate, filtered, and concentrated to a dark solid (5.73 g). It was dissolved in chloroform and ethyl acetate and chromatographed on silica gel with 17% ethyl acetate in hexane to give a yellow solid (2.61 g). A portion (0.24 g) of the solid was recrystallized from toluene (5 mL). The crystals were cooled in an ice bath and filtered off to give light-yellow crystals (0.162 g); mp 218.8°–219.4° C. (dec); MS: m/z=334 (M+1). Analysis for $C_{16}H_{16}ClNO_3Si$: Calculated: C, 57.56; H, 4.83; N, 4.20; Found: C, 57.49; H, 5.01; N, 4.27.

EXAMPLE 42

Methyl(E)-3-(8-chloro-3-methoxy-2,5-dioxo-2,5-dihydro-1H-benzo[b]azepin-4-yl)acrylate Tris(dibenzylideneacetone)dipalladium (O) (0.12 g) in toluene (45 mL) was treated with tri-2-furyl phosphine (0.12 g) under argon. The solution was stirred for 15 minutes at low temperature and treated with methyl propiolate (1.15 mL, 1.09 g) followed by tri-n-butyltin hydride (3.50 mL, 3.78 g). The solution was stirred for 19 hours and then treated with more tris (dibenzylacetone) dipalladium (O) (0.10 g) and tri-2-furylphosphine (0.10 g). The mixture was stirred for 15 minutes and then treated with 8-chloro-4-iodo-3-methoxy-2,5-dioxo-2,5-dihydro-1H-benz[b]azepine (3.63 g) followed by toluene (35 mL). The mixture was heated to 103° C. and it was stirred for 19 hours. The mixture was cooled and concentrated to a dark solid. It was dissolved in chloroform and chromatographed on a silica gel column (8 cm diameter by 17 cm long) using 17% ethyl acetate in hexane to give a pale yellow solid (0.533 g). The solid was recrystallized twice from ethyl acetate (30 mL). The solution was concentrated to 10 mL volume and the crystals were filtered off, washed with cold ethyl acetate, washed with hexane to give a white solid (0.083 g); mp 260.1°–260.5° C. (dec); $^1$H NMR (CDCl$_3$) 7.73 (d,1, J=16.1), 6.71 (d,1, J=16.1) for trans olefin protons; MS: m/z=322 (M+1). Analysis for $C_{15}H_{12}ClNO_5$: Calculated: C, 56.00; H, 3.76; N, 4.35; Found: C, 55.45; H, 3.85; N, 4.13.

EXAMPLE 43

Ethyl(E)-3-(8-chloro-3-methoxy-2,5-dioxo-2,5-dihydro-1H-benzo[b]azepin-4-yl)acrylate A solution of tris(dibenzylideneacetone)dipalladium (O) (0.051 g) in toluene (31 mL) was treated with triphenylphosphine (0.058 g). The solution was stirred under argon at room temperature for 15 minutes and then it was treated with 8-chloro-4-iodo-3-methoxy-2,5-dioxo-2,5-dihydro-1H-benz[b]-azepine (0.97 g) followed by ethyl acrylate (4.3 mL, 4.0 g). The mixture was then treated with triethylamine (0.37 mL, 0.27 g). The mixture was heated to 104° C. for 1.5 hours and then it was cooled to room temperature. Another portion of tris(dibenzylideneacetone)dipalladium (O) (0.025 g) and more triphenyl phosphine (0.029 g) was added to the mixture. The mixture was then treated with more ethyl acrylate (2.8 mL) and it was heated to 105° C. for 1 hour and then it was cooled to room temperature and concentrated to a brown glass. It was dissolved in chloroform and chromatographed on a silica gel column (5.5 cm diameter×20 cm long) using 25% ethyl acetate in hexane to give a pale yellow solid (0.115 g). The solid was recrystallized from ethyl acetate (10 mL) at room temperature to give an off-white solid (0.0712 g); mp 233.8°–234.5° C.; $^1$H NMR (CDCl$_3$) 7.73 (d, 1, J=16), 6.69 (d, 1, J=16) for trans olefin protons; MS: m/z=336 (M+1). Analysis for C$_{16}$H$_{14}$ClNO$_5$: Calculated: C, 57.24; H, 4.20; N, 4.17; Found C, 57.09; H, 4.16; N, 4.09.

EXAMPLE 44 t-butyl-(E)-3-(8-Chloro-3-methoxy-2,5-dioxo-2,5-dihydro-1H-benzo[b]azepin-4-yl)acrylate A solution of tris(dibenzylideneacetone)dipalladium (O) (0.0163 g) in toluene (39 mL) was treated with tri-ortho-tolylphosphine (0.0815 g). The solution was stirred under argon at room temperature for 15 minutes and then it was treated with 8-chloro-4-iodo-3-methoxy-2,5-dioxo-2,5-dihydro-1H-benz[b]azepine (1.22 g) followed by tert-butyl acrylate (7.30 mL, 6.45 g). The mixture was then treated with triethylamine (0.47 mL, 0.34 g) and it was heated to 105° C. for 35 minutes. The mixture was cooled and concentrated to a dark solid. The solid was dissolved in chloroform and chromatographed on a silica gel column (5.5 cm diameter×20 cm long) using 25% ethyl acetate in hexane to give a light yellow solid (0.932 g). A portion of the solid (0.294 g) was dissolved in warm ethyl acetate (5 mL) and then it was concentrated to 3 mL volume. Hexane (1 mL) was added to the solution and crystals formed. The solid was filtered off, washed with cold ethyl acetate, washed with hexane, and dried to give a white solid (0.21 g); mp 213.2°–213.8° C. (dec); $^1$H NMR (CDCl$_3$) 7.67 (d,1, J=16), 6.61 (d,1, J=16) for trans olefin protons; MS: m/z=308 (base peak), 364 (M+1). Analysis for C$_{18}$H$_{18}$ClNO$_5$: Calculated: C, 59.43; H, 4.99; N, 3.85; Found: C, 59.22; H, 4.92; N, 3.79.

EXAMPLE 45

3-(8-Chloro-3-methoxy-2,5-dioxo-2,5-dihydro-1H-benzo[b]azepin-4-yl)acrylic Acid

4-[2-(Tert-butoxycarbonyl)ethenyl]-8-chloro-3-methoxy-2,5-dioxo-2,5-dihydro-1H-benz[b]azepine (0.3455 g) was dissolved in dry methylene chloride (7.5 mL) under argon. The solution was treated with trifluoroacetic acid (7 mL). The solution was stirred at room temperature for 30 minutes. The solution was concentrated under water aspirator vacuum and then it was dried under high vacuum to give a white solid. The solid was dissolved in 125 mL of hot methanol. The solution was filtered and concentrated to 80 mL volume as a white solid formed. It was cooled in an ice bath and the solid was filtered off, washed with cold methanol, and air-dried to give a white solid (0.162 g); mp 281.4°–282.0° C. (dec); $^1$H NMR (d$_6$-DMSO) 7.54 (d,1, J=16), 6.52 (d,1, J=16) for trans olefin protons; MS: m/z=308. Analysis for C$_{14}$H$_{10}$ClNO$_5$: Calculated: C, 54.65; H, 3.28; N, 4.55; Found: C, 54.36; H, 3.14; N, 4.37.

EXAMPLE 46

3-(8-Chloro-3-hydroxy-2,5-dioxo-2,5-dihydro-1H-benzo[b]azepin-4-yl)acrylic Acid

A solution of boron tribromide (0.25 mL, 0.65 g) in methylene chloride (3 mL) was treated with a suspension of 4-[2-(tert-butoxycarbonyl)ethenyl]-8-chloro-3-methoxy-2,5-dioxo-2,5-dihydro-1H-benz[b]azepine (0.2135 g) in methylene chloride (3 mL). The mixture was stirred for 1 hour at room temperature and then it was added to saturated aqueous sodium bicarbonate (18 mL) at room temperature with stirring. The mixture was then acidified to pH 6 with concentrated hydrochloric acid. The mixture was cooled to −10° C. and the solid was filtered off, washed with water, air-dried, and vacuum dried to give a light yellow solid (0.148 g). The solid was dissolved in hot methanol (15 mL). The solution was filtered and concentrated to 7 mL volume. Some water (1 mL) was added and crystals formed slowly. The solid was filtered off, washed with cold methanol, and air-dried to give a light tan solid (0.0712 g); mp 225.2°–226.6° C. (dec); $^1$H NMR (d$_6$-DMSO) 7.70 (d,1, J=16), 6.69 (d,1, J=16) for trans olefin protons; MS: m/z=224 (base peak), 276. Analysis for C$_{13}$H$_8$ClNO$_5$.0.5 H$_2$O: Calculated: C, 53.00; H, 2.77; N, 4.76; Found: C, 52.60; H, 2.66; N, 4.52.

EXAMPLE 47

Ethyl(E)-3-(8-chloro-3-hydroxy-2,5-dioxo-2,5-dihydro-1H-benzo[b]azepin-4-yl)acrylate A solution of 8-Chloro-4-[2-(ethoxycarbonyl)ethenyl]-3-methoxy-2,5-dioxo-2,5-dihydro-1H-benz[b]azepine (0.1009 g) in tetrahydrofuran (2.3 mL) was treated with a solution of lithium hydroxide monohydrate (0.0126 g) in tetrahydrofuran (2.3 mL) and water (0.5 mL) at room temperature. The solution was stirred at room temperature under argon for 68 hours. It was then added to 0.05N hydrochloric acid (10 mL). The resulting solid was filtered off, washed with water, and air-dried to give a light tan solid (0.0803 g). The solid was dissolved in hot ethanol (5 mL). The solution was filtered and treated with water (2 mL). The crystals were filtered off at room tempeature, washed with aqueous ethanol (1:1, v:v) and dried under vaccum to give a light tan solid (0.054 g); mp 177.5°–178.4° C.; $^1$H NMR (d$_6$-DMSO) 7.74 (d,1, J=16) 6.74 (d,1, J=16) for trans olefin protons; MS: m/z=276 (base peak), 322 (M+1). Analysis for C$_{15}$H$_{12}$ClNO$_5$: Calculated: C, 56.00; E, 3.78; N, 3.99; Found: C, 56.55; H, 3.78; N, 3.99.

EXAMPLE 48

(E)-3-(8-Chloro-3-methoxy-2,5-dioxo-2,5-dihydro-1H-benzo[b]azepin-4-yl)-N-phenylacrylamide Oxalyl chloride (0.073 mL) was added dropwise to dimethylformamide (3 mL) at −15° to −20° C. under argon. The suspension was stirred at −15° C. for 20 minutes. The mixture was treated with a solution of 8-chloro-3-methoxy-2,5-dioxo-2,5-dihydro-1H-benz[b]azepine-4-(3-propenoic) acid (0.2341 g) and n-methylmorpholine (0.084 mL, 0.077 g) in dimethylformamide (2 mL) over a 5-minute period. The mixture was stirred at −15° C. for 20 minutes and then aniline (0.077 mL) was added followed by N-methylmorpholine (0.084 mL). The mixture was warmed to 20° C. over a 45-minute period. The mixture was stirred at 20°–24° C. for 3 hours and then it was added to water (30 mL). The resulting solid precipitate was filtered off, washed with water, and vacuum dried to give a yellow solid (0.2133 g). The solid was dissolved in ethyl acetate and passed through a short column (2.5 cm×4 cm long) of silica gel using ethyl acetate. The fraction was concentrated to a yellow foam (0.1503 g). The foam was dissolved in warm ethyl acetate (2 mL) and then it was diluted with ether (1 mL). The resulting crystals were filtered off, washed with ether, and air-dried to give a yellow solid (0.0946 g); mp 215.2°–216.6° C. $^1$H NMR (d$_6$-DMSO) 7.60 (d,1, J=16), 7.03 (d,1, J=16) for trans olefin protons; MS: m/z=383, (M+1) (base peak). Analysis for $C_{20}H_{15}ClN_2O_4$: Calculated: C, 62.35; H, 3.95; N, 7.32; Found: C, 62.35; H, 4.04; N, 7.26.

EXAMPLE 49

(E)-3-(8-Chloro-3-hydroxy-2,5-dioxo-2,5-dihydro-1H-benzo[b]azepin-4-yl)-N-phenylacrylamide 8-Chloro-3-methoxy-4-[2-(phenylaminocarbonyl) ethenyl]-2,5-dioxo-2,5-dihydro-1H-benz[b]azepine (0.39 g) was dissolved in tetrahydrofuran (7.8 mL) under argon. The solution was treated with lithium hydroxide monohydrate (0.043 g) in water (2.1 mL). The solution was stirred at room temperature under argon for 68 hours and then it was concentrated to approximately 3 mL volume. The concentrate was diluted with water (20 mL) and it was acidified to pH 5 with 2N aqueous hydrochloric acid. The resulting solid was filtered off, washed with water, and air-dried to give a yellow solid (0.45 g). The solid was dissolved in warm ethyl acetate (approximately 30 mL) and methanol (approximately 2 mL). The solution was filtered and concentrated to 10 mL volume as a solid formed. The solid was filtered off, washed with cold ethyl acetate, washed with hexane, and air-dried to give a yellow solid (0.29 g); mp 251.8°–252.9° C. (dec); $^1$H NMR (d$_6$-DMSO) 7.81 (d,1, J=15), 7.10 (d,1, J=15) for trans olefin protons; MS: m/z= 122, 276, (lactone); Fab Mass Spec. m/z=369 (positive ion), 367 (negative ion). Analysis for $C_{19}H_{13}N_2O_4$.0.75 $H_2O$: Calculated: C, 59.70; H, 3.82; N, 7.33; Found: C, 59.73; H, 3.59; N, 7.32.

EXAMPLE 50

(E)-3-(8-Chloro-3-methoxy-2,5-dioxo-2,5-dihydro-1H-benzo[b]azepin-4-yl)-N-(4-ethoxyphenyl) acrylamide The title compound was prepared according to the procedure described in Example 48, to afford the desired product as a yellow crystalline solid. Yield 62%; mp 237°–243° C. (dec); $^1$H NMR: (d$_6$-DMSO) 7.53 (d,1, J=16), 6.99 (d,1, J=16) trans olefin protons. MS: m/z=427 (M+1). Analysis for $C_{22}H_{19}ClN_2O_5$.0.75 $H_2O$: Calculated: C, 60.00; H, 4.69; N, 6.36; Found: C, 59.95; H, 4.41; N, 6.22.

EXAMPLE 51

(E)-3-(8-Chloro-3-hydroxy-2,5-dioxo-2,5-dihydro-1H-benzo[b]azepin-4-yl)-N-(4-ethoxyphenyl) acrylamide The title compound was prepared according to the procedure described in Example 49, to afford the desired product as a pale yellow solid. Yield 74%; mp 254°–256° C. (dec); $^1$H NMR: (d$_6$-DMSO) 7.71 (d,1, J=16), 7.11 (d,1, J=16) trans olefin protons; MS: m/z=411 (M+1), 276 (lactone). Analysis for $C_{12}H_{17}ClN_2O_5$.0.5 $H_2O$: Calculated: C, 59.79; H, 4.30; N, 6.64; Found: C, 59.62; H, 4.28; N, 6.51.

EXAMPLE 52

(E)-3-(8-Chloro-3-methoxy-2,5-dioxo-2,,5-dihydro-1H-benzo[b]azepin-4-yl)-N-(2,4-difluorophenyl) acrylamide The title compound was prepared according to the procedure described in Example 48, to afford the desired product as a yellow crystalline solid. Yield 71%; mp 273°–275° C.; $^1$H NMR (d$_6$-DMSO) 7.57 (d,1, J=16) 7.12 (d,1, J=16) trans olefin protons; MS: m/z=419 (M+1). Analysis for $C_{20}H_{13}ClF_2N_2O_4$.2.0 $H_2O$: Calculated: C, 55.95; H, 3.80; N, 6.21; Found: C, 55.61; H, 3.51; N, 6.21.

EXAMPLE 53

(E)-3-(8-Chloro-3-methoxy-2,5-dioxo-2,5-dihydro-1H-benzo[b]azepin-4-yl)-N-methyl-N-phenylacrylamide The title compound was prepared according to the procedure described in Example 48 to afford the desired product as a pale yellow crystalline solid. Yield 83%; mp 192°–194° C.; $^1$H NMR (d$_6$-DMSO) 7.41 (d,1, J=16), 6.60 (d,1, J=16) trans olefin protons; MS: m/z=397 (base peak)(M+1). Analysis for $C_{21}H_{17}ClN_2O_4$.0.75 $H_2O$: Calculated: C, 61.47, H, 4.54; N, 6.82; Found: C, 61.67; H, 4.43; N, 6.83.

EXAMPLE 54

(E)-3-(8-Chloro-3-hydroxy-2,5-dioxo-2,5-dihydro-1H-benzo[b]azepin-4-yl)-N-methyl-N-phenylacrylamide 8-Chloro-4-[2-(phenyl-N-methylaminocarbonyl)ethenyl]-3-methoxy-2,5-dioxo-2,5-dihydro-1H-benz[b]azepine (0.150 g) was suspended in methylene chloride (10 mL) under nitrogen. This suspension was treated in one portion with boron tribromide (285 mg, 1.07 μL) via syringe at ambient temperature. The mixture immediately went from a buff suspension to a rust red mixture. Stirring was continued for one hour. The mixture was then treated with saturated aqueous sodium bicarbonate (10 mL) and the pH of the mixture was then adjusted to pH 3 with concentrated hydrochloric acid and the resulting buff colored suspension was stirred for an additional hour. The solid product was filtered off and washed with cold water and dried. The crude product was dissolved in warm ethyl acetate (15 mL) and hexane was added gradually to precipitate the product. The product was filtered off and dried under vaccum to afford the desired product 84 mg. Yield 58%; $^1$H NMR (d$_6$-DMSO) 7.63 (d,1, J=16), 6.80 (d,1, J=16) trans olefin protons; MS: m/z=383 (M+1). Analysis for $C_{20}H_{15}ClN_2O_4$: Calculated: C, 62.75; H, 3.95; N, 7.32; Found: C, 62.45; H, 3.94; N, 7.08.

EXAMPLE 55

(E)-3-(8-Chloro-3-methoxy-2,5-dioxo-2,5-dihydro-1H-benzo[b]azepin-4-yl)-N-(2-isopropylphenyl) acrylamide The title compound was prepared according to the procedure described in Example 48 to afford the desired product as a yellow solid. Yield 53%; mp 2.35°–240° C. (dec); $^1$H NMR (d$_6$-DMSO) 7.53 (d,1, J=16), 7.09 (d,1, J=16) trans olefin protons; MS: m/z=425 (M+1). Analysis for C$_{23}$H$_{21}$ClN$_2$O$_4$.0.75 H$_2$O: Calculated: C, 63.01; H, 5.17; N, 6.35; Found: C, 63.05; H, 5.25;.N, 5.96.

EXAMPLE 56

(E)-3-(8-Chloro-3-hydroxy-2,5-dioxo-2,5-dihydro-1H-benzo[b]azepin-4-yl)-N-(2-isopropylphenyl)acrylamide The title compound was prepared according to the procedure described in Example 49 to afford the desired product as a tan solid. Yield 82%; mp 248°–250° C. (dec); $^1$H NMR (d$_6$-DMSO) 7.70 (d,1, J=15) 7.14 (d,1, J=15) trans olefin protons; MS: m/z=276 (lactone), 411 (M+1). Analysis for C$_{22}$H$_{19}$ClN$_2$O$_4$.0.75 H$_2$O: Calculated: C, 62.27; H, 4.87; N, 6.60; Found: C, 62.59; H, 4.96; N, 6.25.

EXAMPLE 57

(E)-3-(8-Chloro-3-hydroxy-2,5-dioxo-2,5-dihydro-1H-benzo[b]azepin-4-yl)-N-o-tolylacrylamide The title compound was prepared according to the procedure described in Example 49 to afford the desired product as a tan solid. Yield 64%; mp 242°–248° C. (dec); $^1$H NMR (d$_6$-DMSO) 7.71 (d,1, J=16), 7.06 (d,1, J=16); MS: m/z=276 (lactone), 383 (M+1). Analysis for C$_{20}$H$_{15}$ClN$_2$O$_4$.1.5 H$_2$O: Calculated: C, 58.61; H, 4.43; N, 6.83; Found: C, 58.59; H, 4.12; N, 6.96.

EXAMPLE 58 t-butyl-(E)-3-(8-Chloro-3-methoxy-2,5-dioxo-2,5-dihydro-1H-benzo[b]azepin-4yl)acrylate The title compound was prepared in the manner described in Example 44 using the 8-chloro-4-iodo-3-methoxy-2,5-dioxo-2,5-dihydro-1H-benz[b]azepine (2.18 g) and tert-butylmethacrylate (17.1 g) in toluene (70 mL) with tris(dibenzylideneacetone)dipalladium (O) (0.10 g) and tri-orthotolylphosphine (0.13 g). The mixture was treated with triethylamine (0.84 mL, 0.61 g) and heated at 104° C. for 3.7 hours. The mixture was concentrated to a dark solid which was dissolved in chloroform and chromatographed on a silica gel column (5.5 cm diameter×18 cm long) using 25% ethyl acetate in hexane. Concentration of the main fraction gave a white solid (0.77 g). A portion (0.21 g) of the solid was dissolved in hot ethyl acetate (7 mL). The solution was diluted with hexane (5 mL) and the crystals formed at room temperature. The solid was filtered off, washed with ethyl acetate, washed with hexane, and air-dried to give white crystals (0.11 g); mp=189.1°–199.8° C.; $^1$H NMR(CDCl$_3$) 7.27 (s,1) for olefin proton; MS: m/z=322 (base peak), 378 (M+1). Analysis for C$_{19}$H$_{20}$ClNO$_5$: Calculated: C, 60.40; H, 5.34; N, 3.71; Found: C, 60.18; H, 5.43; N, 3.72.

EXAMPLE 59

(E)-3-(8-Chloro-3-hydroxy-2,5-dioxo-2,5-dihydro-1H-benzo[b]azepin-4-yl)-2-methylacrylic Acid 4-[2-(Tert-butoxycarbonyl)propenyl]-8-chloro-3-methoxy-2,5-dioxo-2,5-dihydro-1H-benz[b]azepine (0.32 g) in methylene chloride (4 mL) was added to boron tribromide (0.33 mL) in methylene chloride (4 mL) at room temperature under argon. The mixture was stirred at room temperature for 1.5 hours and then it was added to saturated aqueous sodium bicarbonate (24 mL). The mixture was stirred for 10 minutes and then it was acidified to pH 5 with concentrated hydrochloric acid. The suspension was cooled to −10° C. and the solid was filtered off, washed with water, and vacuum dried to give a white solid (0.16 g). The solid was dissolved in hot methanol (60 mL), filtered, and concentrated to 10 mL volume. The suspension was cooled in an ice bath and the solid was filtered off, washed with cold methanol, and vacuum dried to give a white solid (0.1051 g); mp=242.2°–243.0° C. (dec); $^1$H NMR (d$^6$:DMSO) 7.48 (s,1) for olefin proton; MS: m/z=264, 290, 308 (M+1). Analysis for C$_{14}$H$_{10}$ClNO$_5$: Calculated: C, 54.65; H, 3.28; N, 4.55; Found: C, 54.85; H, 3.48; N, 4.50.

EXAMPLE 60

(E)-3-(8-Chloro-3-methoxy-2,5-dioxo-2,5-dihydro-1H-benzo[b]azepin-4-yl)-2-methylacrylic Acid 4-[2-(Tert-butoxycarbonyl)propenyl]-8-chloro-3-methoxy-2,5-dioxo-2,5-dihydro-1H-benz[b]azepine (0.35 g) in methylene chloride (7 mL) was treated with trifluoroacetic acid. The solution was stirred under argon at room temperature for 40 minutes and then it was concentrated to a white solid. The solid was dissolved in hot methanol (30 mL). The solution was filtered and concentrated to 7 mL volume as a solid formed. The solid was filtered off, washed with cold methanol, and air-dried to give a white solid (0.0748 g); mp=277.4°–278.6° C. (dec); $^1$H NMR (d$^6$-DMSO) 7.17 (s,1) for olefin proton; MS: m/z=304, 322 (base peak)(M+1). Analysis for C$_{15}$H$_{12}$ClNO$_5$: Calculated: C, 56.00; H, 3.76; N, 4.35; Found: C, 55.86; H, 3.82; N, 4.32.

EXAMPLE 61

(E)-3-(8-Chloro-3-methoxy-2,5-dioxo-2,5-dihydro-1H-benzo[b]azepin-4-yl)-2-methyl-N-phenylacrylamide The title compound was prepared in the manner given in Example 48 using 8-chloro-3-methoxy-2,5-dioxo-2,5-dihydro-1H-benz[b]azepine-4-(2-methyl-3-propenoic) acid (0.62 g). Similar workup gave a light-yellow solid (0.34 g). The solid was dissolved in hot ethyl acetate (20 mL). The solution was concentrated to 10 mL volume and crystals formed slowly over an 18 hour period. The solid was filtered off, washed with cold ethyl acetate, washed with hexane, and air-dried to give light-yellow crystals (0.1532 g); mp 225.8°–227.2° C.; $^1$H NMR(d$^6$-DMSO) 6.99 (s,1) for olefin proton; MS: m/z=397 (M+1). Analysis for C$_{21}$H$_{17}$ClN$_2$O$_4$.0.05 H$_2$O: Calculated: C, 62.15; H, 4.47; N, 6.90; Found: C, 62.35; H, 4.74; N, 6.46.

EXAMPLE 62

The 3-hydroxy version of Example 61 may readily be prepared according to the procedures described herein.

EXAMPLE 63

(E)-N-Benzyl-3-(8-chloro-3-methoxy-2,5-dioxo-2,-1H-benzo[b]azepin-4-yl)acrylamide The title compund was prepared according to the procedure described in Example 48, to afford the desired product; mp 228.3°–230.1° C.; MS: m/z=397 (M+1). Analysis for C$_{21}$H$_{17}$N$_2$O$_4$Cl: Calculated: C, 63.56; H, 4.32; N, 7.06; Found: C, 62.50; H, 4.39; N, 6.91.

EXAMPLE 64

Dimethyl 2-(8-chloro-3-hydroxy-2,5-dioxo-2,5-dihydro-1H-benzo[b]azepin-4-ylmethylene)succinate The title compound was prepared from 8-chloro-4-iodo-3-methoxy-2,5-dioxo-2,5-dihydro-1H-benz[b]azepine (1.26 g) using the method given in Example 44. Similar workup and purification by chromatography gave a pale yellow oil (1.05 g) which was dissolved in hot ethyl acetate (8 mL). The solution was cooled to room temperature and the solid was filtered off, washed with ethyl acetate, and washed with hexane and air-dried to give white crystals (0.584 g); mp=159.5°–160.1° C.; MS: m/z=394(M+1). Analysis for $C_{18}H_{16}ClNO_7$: Calculated: C, 54.90; H, 4.10; N, 3.56; Found: C, 54.94; H, 4.24; N, 3.47.

EXAMPLE 65

1-butyl 2-(8-Chloro-3-methoxy-2,5-dioxo-2,5-dihydro-1H-benzo[b]azepin-4-ylmethyl)acrylate The title compound was obtained as a byproduct in the chromatography to purify the product of Example 58. The fraction was concentrated to give a white solid (0.1422 g). It was recrystallized from ethyl acetate (2 mL) to give a white solid (0.0982 g); mp=141.7°–142.0° C.; MS: m/z=322 (base peak). Analysis for $C_{19}H_{20}ClNO_5$: Calculated: C, 60.40; H, 5.34; N, 3.71; Found: C, 60.26; H, 5.38; N, 3.70; $^1$H NMR (CDCl$_3$), 6.05 (s,1, J=0.7), 5.34 (s,1, J=0.7) for general olefin protons.

The following pages present the formulae for the various generic structures utilized to prepare the compounds within the scope of the invention from readily prepared and/or commercially available starting materials as described herein. In addition, the tables presented below show certain physical data and yields for some of the examples presented herein. Compounds described as carbamoyls in the specification are named as acrylamides according to IUPAC nomenclature wherein an amine is reacted with an acrylic acid to form the acrylamides of the present invention. The above examples are understood to be non-limiting. The preferred synthetic routes are shown in the above examples. Applicants preferred utility is the prevention of ischemic damage following a stroke.

FORMULAE

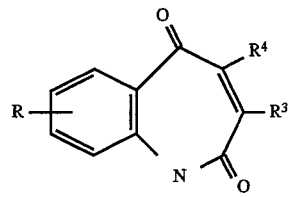

I

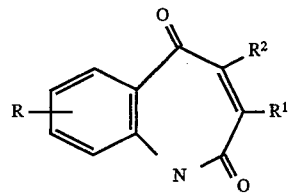

II

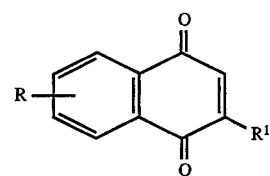

III

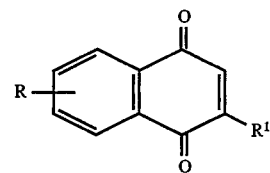

IV

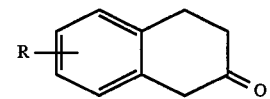

V

TABLE 1

The following examples were prepared generally as set forth in Example 3, using appropriate corresponding precursors to make the compounds listed.

| Ex. # | Yield | m.p. | MS(Cl) | NMR(d6-DMSO) | Analysis(experiment/theory) |
|---|---|---|---|---|---|
| 7 | 91% | 310–312 | 345(M+1) | 7.33(m, 1H), 7.50(m, 3H), 7.92(d, 1H, J=8.7Hz), 8.25(m, 2H), 10.60(brs, 1H), 11.90(s, 1H) | C=55.40/55.75, H=2.54/2.63, N=8.05/8.13 $C_{16}H_9ClN_2O_5$ |
| 9 | 61% | 311–312 | 345(M+1) | 7.33(m, 1H), 7.55(m, 1H), 7.68(m, 2H), 7.94(d, 1H, J=8.7Hz) 8.09(m, 1H), 8.20(m, 1H), 10.72 (brs, 1H), 11.91(s, 1H) | C=55.58/55.75, H=2.56/2.63, N=8.21/8.13 $C_{16}H_9ClN_2O_5$ |
| 12 | 27% | 192–193 | 392(M+1) | 6.98(d, 2H, J=7.9Hz), 7.07(d, 2H, J=8.5Hz), 7.21(m, 3H), 7.32(d, 1H, J=8.5Hz), 7.42(m, 2H), 7.51 (s, 1H), 7.87(d, 1H, J=8.6Hz), 10.33(s, 1H), 11.83(s, 1H) | C=67.13/67.4, H=3.36/3.6, N=3.55/3.57 $C_{22}H_{14}ClNO_4$ |
| 17 | 43% | 257–259 | 316(M+1) | 6.70(d, 2H, J=8.4Hz), 6.98(d, 2H, J=8.4Hz), 7.27(d, 1H, J=8.6Hz), 7.44(s, 1H), 7.78(d, 1H, J=8.6Hz), 9.38(s, 1H), 10.04(s, 1H), 11.71(s, 1H) | C=59.68/59.68, H=3.54/3.35, N=4.22/4.35 $C_{16}H_{10}ClNO_4$—0.35$H_2O$ |

TABLE 1-continued

The following examples were prepared generally as set forth in Example 3, using appropriate corresponding precursors to make the compounds listed.

| Ex. # | Yield | m.p. | MS(CI) | NMR(d6-DMSO) | Analysis(experiment/theory) |
|---|---|---|---|---|---|
| 21 | 87% | 288–290 (dec.) | 404(M+1) | 7.35(m, 3H), 7.58(m, 3H), 7.70(m, 5H), 7.91(d, 1H, J=8.7Hz), 10.57(s, 1H), 11.87(s, 1H) | C=67.22/67.21, H=3.33/3.63, N=3.30/3.41 $C_{23}H_{14}ClNO_4$—0.4$H_2O$ |
| 22 | 12% | 270–272 | 344(M+1) | 6.00(s, 2H), 6.64(d, 1H, J=8.0Hz) 6.74(s, 1H), 6.89(d, 1H, J=8.0Hz) 7.3(d, 1H, J=8.7Hz), 7.48(s, 1H), 7.84(d, 1H, J=8.7Hz), 10.24(s, 1H), 11.77(s, 1H) | C=57.82/57.89, H=3.13/3.14, N=3.83/3.97 $C_{17}H_{10}ClNO_5$—0.5$H_2O$ |

TABLE 2

The following Examples were made generally as set forth in Example 6, using appropriate corresponding precursors to make the compounds listed.

| Ex. # | Yield | m.p. | MS(CI) | NMR(d6-DMSO) | Analysis(experiment/theory) |
|---|---|---|---|---|---|
| 8 | 12% | 191–193 (dec.) | 314(M+1) | 3.65(s, 3H), 7.25(M, 7H), 7.61(d, 1H, j=8,5Hz) | C=64.59/64.71, H=3.78/3.90 N=4.43/4.44 $C_{17}H_{12}ClNO_3$—0.1$H_2O$ |
| 10 | 61% | not taken | 359(M+1) | 3.71(s, 3H), 7.32(m, 1H), 7.43(m, 1H), 7.72(m, 3H), 8.13(m, 1H), 8.22(m, 1H), 11.63(s, 1H) | not done. |
| 11 | 57% | 209–210.5 | 406(M+1) | 3.67(s, 1H), 6.98(d, 2H), 7.08(d, 2H), 7.18(m, 1H), 7.31(m, 3H), 7.43(m, 3H), 7.62(d, 1H), 11.53(s, 1H) | C=67.14/67.17, H=3.82/4.00 N=3.36/3.41 $C_{23}H_{16}ClNO_4$—0.3$H_2O$ |
| 13 | 56% | 234–235.5 | 358(M+1) | 1.42(m, 3H), 3.71(s, 3H), 4.05 (m, 2H), 6.92(d, 2H, J=8.6Hz), 7.21(d, 2H, J=3.6Hz), 7.25(m, 3H) 7.70(d, 1H, J=8.4Hz), 9.66(s, 1H) | C=62.64/62.83, H=4.32/4.61 N=3.92/3.85 $C_{19}H_{16}ClNO_4$—0.3$H_2O$ |
| 18 | 39% | 213–214 | 427(M+1) | 1.02(brs, 12H), 2.98(m, 2H), 3.64(s, 5H), 7.17(d, 2H, J=8.0Hz), 7.36(m, 4H), 7.60(d, 1H, J=8.5Hz), 11.51(s, 1H) | C=67.10/67.10, H=6.47/6.40 N=6.41/6.52 $C_{24}H_{27}ClN_2O_3$—0.15$H_2O$ |
| 20 | 16% | 154–156 | 418(M+1) | 3.71(s, 3H), 7.32(d, 1H, J=8.7Hz), 7.42(m, 3H), 7.59(m, 2H), 7.67(m, 2H), 7.76(m, 4H), 11.59(s, 1H) | C=68.56/68.69, H=3.74/3.89 N=3.28/3.34 $C_{24}H_{16}ClNO_4$—0.1$H_2O$ |
| 23 | 30% | 218–220 | 353(M+1) | 3.66(s, 3H), 4.07(s, 2H), 7.33(m, 6H), 7.62(d, 1H, J=8.5Hz), 11.55(s, 1H) | |
| 32 | 48% | not taken | 315(M+1) | 3.78(s, 3H), 7.34(m, 1H), 7.45(m, 1H), 7.72(d, 1H, j=8.5Hz), 7.88(m, 1H), 8.24(d, 1H, j=8.1Hz) 8.77(m, 2H), 11.72(s, 1H) | |
| 34 | 45% | not taken | 315(M+1) | 3.66(s, 3H), 7.36(m, 4H), 7.64(d, 1H, J=8.5), 7.84(m, 1H), 8.56(m, 1H), 11.58(S, 1H) | |
| 36 | 18% | not taken | 345(M+1) | 3.69(s, 3H), 3.74(s, 3H), 6.78(d, 1H, J=8.2Hz), 7.03(d, 1H, J=7.3Hz), 7.35(d, 1H, J=8.2Hz), 7.39(s, 1H), 7.64(d, 1H, J=8.4Hz), 7.7(m, 1H), 11.54(s, 1H) | |
| 38 | 64% | not taken | 308(M+1) | 1.19(t, 3H, j=7.0), 3.77(m, 5H), 4.14(d, 1H, j=2.3), 4.44(d, 1H, j=2.2), 7.33(m, 2H), 7.60(d, 1H, j=8.3Hz) | |

TABLE 3

The following Examples were prepared generally as set forth in Example 14, using appropriate corresponding precursors to make the compounds listed

| Ex. # | yield | m.p. | MS(Cl) | NMR(d6-DMSO) | Analysis(experiment/theory) |
|---|---|---|---|---|---|
| 14 | 59% | 193–196 | 300(M+1) | 7.18(m, 2H), 7.31(m, 4H), 7.52(s, 1H), 7.87(d, 1H, J=8.7Hz), 10.28(brs, 1H), 11.81(s, 1H) | C=62.82/62.98, H=3.33/3.50, N=4.67/4.59 $C_{16}H_{10}ClNO_3$—0.3$H_2O$ |
| 15 | 52% | 252–254 | 330(M+1) | 3.77(s, 3H), 6.91(m, 2H), 7.14(m, 2H), 7.31(m, 1H), 7.49(d, 1H, J=2.0Hz), 7.83(d, 1H, J=8.6Hz), 10.20(brs, 1H), 11.77(s, 1H) | C=61.43/61.59, H=3.58/3.71, N=4.17/4.25 $C_{17}H_{12}ClNO_4$—0.1$H_2O$ |
| 16 | 70% | 230–231 | 330(M+1) | 3.74(s, 3H), 6.74(m, 2H), 6.88(m, 1H), 7.30(m, 2H), 7.50(d, 1H, J=1.6Hz), 7.87(d, 1H, J=8.6Hz), 10.27(brs, 1H), 11.81(s, 1H) | C=61.30/61.59, H=3.65/3.71, N=4.32/4.25 $C_{17}H_{12}ClNO_4$—0.1$H_2O$ |

TABLE 4

The following Examples were prepared generally as set forth in Example 33, using appropriate corresponding precursors to make the compounds listed.

| Ex. # | Yield | m.p. | MS(Cl) | NMR(d6-DMSO) | Analysis(experiment/theory) |
|---|---|---|---|---|---|
| 19 | 79% | 170–172 | 413(M+1) | 1.39(brs, 12H), 3.69(bm, 2H), 4.39(s, 2H), 7.28(d, 2H, J=7.8Hz), 7.34(d, 1H, J=8.7Hz), 7.56(s, 1H), 7.64(d, 1H, J=7.0Hz), 7.89(d, 1H, J=8.7Hz), 9.23(brs, 1H), 10.41(brs, 1H), 11.90(s, 1H) | C=59.96/59.8, H=5.86/5.96, N=5.74/5.96 $C_{23}H_{25}ClN_2O_2$—1.8HCl—0.1$(C_2H_5)_2O$ |
| 31 | 92% | 300–301 (Dec.) | 301(M+1) | 7.36(dd, 1H, J1=8.7, J2=1.9), 7.99(D, 1H, J=8.7), 8.06(M, 1H), 8.42(D, 1H, J=8.0), 8.86(M, 2H), 11.99(S, 1H) | C=47.43/47.21, H=2.81/2.64, N=7.23/7.34 $C_{15}H_9ClN_2O_3$—1.0HBr |
| 33 | 97% | 272–273 | 301(M+1) | 7.29(m, 2H), 7.54(m, 1H), 7.84(m, 1H), 8.24(m, 1H), 8.60(d, 1H, J=5.8), 11.23(s, 1H) | C=45.91/45.76, H=2.48/2.66, N=6.68/7.11 $C_{15}H_9ClN_2O_3$—1.15HBr |
| 35 | 85% | 232–233 (dec.) | 331(M+1) | 3.93(s, 3H), 6.93(d, 1H, J=8.3Hz), 7.18(d, 1H, J=7.7Hz), 7.34(d, 1H), 7.42(s, 1H), 7.92(m, 2H), 11.62(s, 1H) | C=46.68/46.68, H=2.99/2.94, N=6.74/6.80 $C_{16}H_{11}ClN_2O_4$—1.0HBr |

What is claimed is:

1. A pharmaceutical composition comprising an effective amount of a compound of formula I

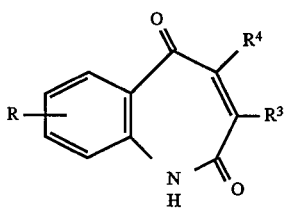

wherein

R denotes 0–3 substituents on the benz-ring selected independently from halo, trifluoromethyl and cyano;

$R^3$ is hydroxy, (1–6C)alkyloxy (which may bear a carboxy or (1–3C)alkoxycarbonyl substituent) or $NR^aR^b$ in which $R^a$ and $R^b$ are independently selected from hydrogen, (1–6C)alkyl, (2–6C)alkenyl, (3–7C)cycloalkyl, (3–7C)cycloalkyl(1–6C)alkyl, aryl, aryl(1–6C)alkyl, heteroaryl, heteroaryl(1–6C)alkyl and $CH_2Y$ in which Y is $(CHOH)_nCH_2OH$ or $(CH_2)_nR^c$ (wherein n is an integer from 1 to 5) and in which $R^a$ and $R_b$ (except when $CH_2Y$) independently may bear a $COR^c$ substituent; or $NR^aR^b$ forms a pyrrolyl, pyrrolinyl, pyrrolidinyl, piperidino, piperazinyl, morpholino, thiomorpholino (or S-oxide) or perhydroazepinyl ring which may further bear one or more (1–6C)alkyl, phenyl, phenyl (1–4C)alkyl, phenoxy or phenyl(1–4C)alkyl substituents;

$R^4$ is (2–6C)alkenyl, (2–6C)alkynyl, aryl or heteroaryl and $R^4$ independently may bear $COR^c$; —OH or —O(1–4C) alkyl; (1–4C) alkyl, -(1–4C)alkylcarboxy (1–4C)alkyl, aryl or —Si— and wherein $R^c$ is hydroxy, (1–4C)alkoxy, or $NR^dR^e$ in which $R^d$ and $R^e$ are independently selected from hydrogen,(1–3C) alkyl, benzyl or phenyl wherein the aryl portion may be unsubstituted or substituted with halogen, (1–4C)alkyl or (1–5C)O—; or $NR^dR^e$ forms a pyrrolyl, pyrrolinyl, pyrrolidinyl, piperidino, piperazinyl (which may bear a (1–3C)alkyl or benzyl substituent at the 4-position), morpholino, thiomorpholino (or S-oxide) or perhydroazepinyl ring;

and wherein each aryl moiety is selected from a phenyl radical or an ortho-fused bicyclic carbocyclic radical having nine to ten ring atoms in which at least one ring is aromatic; and each heteroaryl moiety is a radical attached via a ring carbon of a monocyclic aromatic ring containing five ring atoms consisting of carbon and one to four heteroatoms selected from oxygen, sulfur and nitrogen, or containing six ring atoms consisting of carbon and one or two nitrogens;

and in which an aryl or heteroaryl portion of $R^3$ or $R^4$ may bear one or more halo, trifluoromethyl, (1–6C)alkyl, (2–6C)alkenyl, phenyl, phenyl(1–4C)alkyl, hydroxy, (1–6C)alkoxy, phenoxy, phenyl(1–4C)alkoxy, nitro, amino, (1–4C)acylamino, trifluoroacetylamino, carboxy, (1–3C)alkoxy-carbonyl or a phenyl carbonyl group; a 1,3 dioxolo group; a -(1–4C)alkylNRR' wherein R or R' is H or (1–4C)alkyl; a -(1–4C)alkylCN or cyano substituents;

or a pharmaceutically acceptable salt thereof and a pharmaceutically acceptable excipient.

2. A pharmaceutical composition according to claim 1 wherein the benz-ring on formula I bears a substituent R at the 8-position and R is chosen from a halo group or a pharmaceutically acceptable salt or crystalline form thereof.

3. A pharmaceutical composition according to claim 1 wherein the benz-ring on formula I bears a substituent R at the 8-position and R is chosen from a halo group and wherein $R^3$ is chosen from a hydroxy, methoxy or ethoxy group or a pharmaceutically acceptable salt or crystalline form thereof.

4. A pharmaceutical composition according to claim 1 wherein the benz-ring on formula I bears a substituent R at the 8-position and is selected from chloro and wherein $R^3$ is chosen from hydroxy or methoxy or a pharmaceutically acceptable salt or crystalline form thereof.

5. A pharmaceutical composition according to claim 1 wherein the compound is selected from:

8-Chloro-3-methoxy-4-phenyl-1H-benzo(b)azepine-2,5-dione,

8-Chloro-3-hydroxy-4-(3-nitrophenyl)-1H-benzo(b)azepine-2,5-dione,

8-Chloro-3-hydroxy-4-(4-phenoxyphenyl)-1H-benzo(b)azepine-2,5-dione,

8-Chloro-4-(4-ethoxyphenyl)-3-methoxy-1H-benzo(b)azepine-2,5-dione,

8-Chloro-3-methoxy-4-(4-phenoxyphenyl)-1H-benzo(b)azepine-2,5-dione,

8-Chloro-3-hydroxy-4-phenyl-1H-benzo(b)azepine-2,5-dione,

8-Chloro-3-hydroxy-4-(4-methoxyphenyl)-1H-benzo(b)azepine-2,5-dione,

8-Chloro-3-hydroxy-4-(3-methoxyphenyl)-1H-benzo(b)azepine-2,5-dione,

8-Chloro-3-hydroxy-4-(4-hydroxyphenyl)-1H-benzo(b)azepine-2,5-dione,

8-Chloro-3 -methoxy-4-(2-thienyl)-1H-benzo(b)azepine-2,5-dione,

8-Chloro-3-methoxy-4-phenylethynyl-1H-benzo(b)azepine-2,5-dione,

8-Chloro-4-(4-[(diisopropylamino)methyl]phenyl}-3-methoxy-1H-benzo(b)azepine-2,5-dione, 4-(4-Benzoylphenyl)-8-chloro-3-methoxy-1H-benzo(b)azepine-2,5-dione, 4-Benzo[1,3]dioxol-5-yl-8-chloro-3-hydroxy-1H-benzo(b)azepine-2,5-dione, 8-Chloro-4-[4-(diisopropylamino)methyl]phenyl)-3-hydroxy-1H-benzo(b)azepine-2,5-dione, 8-Chloro-4-furan-2-yl-3-methoxy-1H-benzo(b)azepine-2,5-dione, 8-Chloro-4-furan-2-yl-3-hydroxy-1H-benzo(b)azepine-2,5-dione, 8-Chloro-3-hydroxy-4-(2-thienyl)-1H-benzo(b)azepine-2,5-dione, 4-(4-Benzoylphenyl)-8-chloro-3-hydroxy-1H-benzo(b)azepine-2,5-dione,

[4-(8-Chloro-3-methoxy-2,5-dioxo-2,5-dihydro-1H-benzo(b)azepine-4-yl)phenyl]acetonitrile, 8-Chloro-3-hydroxy-4-(pyridine-3-carbonyl)-1H-benzo(b)azepine-2,5-dione, 4-Acetyl-8-chloro-3-hydroxy-1H-benzo(b)azepine-2,5-dione, 8-Chloro-4-(2-ethoxyvinyl)-3-methoxy-1H-benzo(b)azepine-2,5-dione, 8-Chloro-3-hydroxy-4-pyridin-2-yl-1H-benzo(b)azepine-2,5-dione, 8-Chloro-3-methoxy-4-trimethylsilanylethynyl-1H-benzo(b)azepine-2,5-dione, 8-Chloro-3-hydroxy-4-thiophen-3-yl-1H-benzo(b)azepine-2,5-dione, Methyl (E)-3-(8-chloro-3-methoxy-2,5-dioxo-2,5-dihydro-1H-benzo[b]azepin-4-yl)acrylate, 8-Chloro-3-hydroxy-4-(6-methoxypyridin-2-yl)-1H-benzo[b]azepine-2,5-dione, Ethyl (E)-3-(8-chloro-3-methoxy-2,5-dioxo-2,5-dihydro-1H-benzo[b]azepin-4-yl)acrylate, t-Butyl (E)-3-(8-Chloro-3-methoxy-2,5-dioxo-2,5-dihydro-1H-benzo[b]azepin-4-yl)acrylate, 3-(8-Chloro-3-methoxy-2,5-dioxo-2,5-dihydro-1H-benzo[b]azepin-4-yl)acrylic acid, 3-(8-Chloro-3-hydroxy-2,5-dioxo-2,,5-dihydro-1H-benzo[b]azepin-4-yl)acrylic acid, Ethyl (E)-3-(8-chloro-3-hydroxy-2,5-dioxo-2,5-dihydro-1H-benzo[b]azepin-4-yl)acrylate, (E)-3-(8-Chloro-3-methoxy-2,5-dioxo-2,5-dihydro-1H-benzo[b]azepin-4-yl)-N-phenylacrylamide, (E)-3-(8-Chloro-3-methoxy-2,5-dioxo-2,5-dihydro-1H-benzo[b]azepin-4-yl)-N-(4-ethoxyphenyl)acrylamide, (E)-3-(8-Chloro-3-methoxy-2,5-dioxo-2,,5-dihydro-1H-benzo[b]azepin-4-yl)-N-(2,4-difluorophenyl)acrylamide, (E)-3-(8-Chloro-3-methoxy-2,5-dioxo-2,5-dihydro-1H-benzo[b]azepin-4-yl)-N-methyl-N-phenylacrylamide, (E)-3-(8-Chloro-3-methoxy-2,5-dioxo-2,5-dihydro-1H-benzo[b]azepin-4-yl)-N-(2-isopropylphenyl)acrylamide, t-Butyl (E)-3-(8-Chloro-3-methoxy-2,5-dioxo-2,5-dihydro-1H-benzo[b]azepin-4yl)acrylate, (E)-3-(8-Chloro-3-hydroxy-2,5-dioxo-2,5-dihydro-1H-benzo[b]azepin-4-yl)-N-methyl-N-phenylacrylamide, (E)-3-(8-Chloro-3-hydroxy-2,5-dioxo-2,5-dihydro-1H-benzo[b]azepin-4-yl)-2-methylacrylic acid, (E)-N-Benzyl-3-(8-chloro-3-methoxy-2,5-dioxo-2,5-dihydro-1H-benzo[b]azepin-4-yl)acrylamide, (E)-3-(8-Chloro-3-hydroxy-2,5-dioxo-2,5-dihydro-1H-benzo[b]azepin-4-yl)-N-phenylacrylamide, (E)-3-(8-Chloro-3-methoxy-2,5-dioxo-2,5-dihydro-1H-benzo[b]azepin-4-yl)-2-methylacrylic acid, t-Butyl (E)-2-(8-chloro-3-methoxy-2,5-dioxo-2,5-dihydro-1H-benzo[b]azepin-4-ylmethyl)acrylate, (E)-3-(8-Chloro-3-hydroxy-2,5-dioxo-2,5-dihydro-1H-benzo[b]azepin-4-yl)-N-(2-isopropylphenyl)acrylamide, (E)-3-(8-Chloro-3-hydroxy-2,5-dioxo-2,5-dihydro-1H-benzo[b]azepin-4-yl)-N-(4-ethoxyphenyl)acrylamide, (E)-3-(8-Chloro-3-hydroxy-2,5-dioxo-2,5-dihydro-1H-benzo[b]azepin-4-yl)-N-o-tolylacrylamide, or Dimethyl2-(8-chloro-3-hydroxy-2,5-dioxo-2,5-dihydro-1H-benzo[b]azepin-4-ylmethylene)succinate, or a pharmaceutically acceptable salt or crystalline form thereof.

6. A method of treating perinatal asphyxia, epilepsy, pain, drug and alcohol withdrawal symptoms or tolerance and dependence on opiate analgesics comprising administering to a patient in need of treatment thereof a therapeutically effective amount of a pharmaceutical composition according to claim 1.

7. A method of treating perinatal asphyxia, epilepsy, pain, drug and alcohol withdrawal symptoms or tolerance and dependence on opiate analgesics comprising administering to a patient in need of treatment thereof a therapeutically effective amount of a pharmaceutical composition according to claim 2.

8. A method of treating perinatal asphyxia, epilepsy, pain, drug and alcohol withdrawal symptoms or tolerance and dependence on opiate analgesics comprising administering to a patient in need of treatment thereof a therapeutically effective amount of a pharmaceutical composition according to claim 3.

9. A method of treating perinatal asphyxia, epilepsy, pain, drug and alcohol withdrawal symptoms or tolerance and dependence on opiate analgesics comprising administering to a patient in need of treatment thereof a therapeutically effective amount of a pharmaceutical composition according to claim 4.

10. A method of treating perinatal asphyxia, epilepsy, pain, drug and alcohol withdrawal symptoms or tolerance and dependence on opiate analgesics comprising administering to a patient in need of treatment thereof a therapeutically effective amount of a pharmaceutical composition according to claim 5.

11. A process for producing a compound of the Formula I:

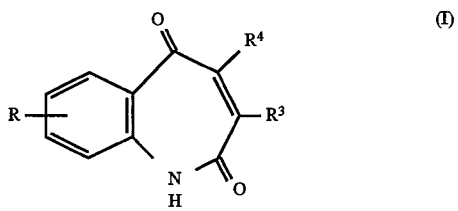

wherein

R denotes 0–3 substituents on the benz-ring selected independently from halo, trifluoromethyl and cyano;

$R^3$ is hydroxy, (1–6C)alkyloxy (which may bear a carboxy or (1–3C)alkoxycarbonyl substituent) or $NR^aR^b$ in which $R^a$ and $R^b$ are independently selected from hydrogen, (1–6C)alkyl, (2–6C)alkenyl, (3–7C)cycloalkyl, (3–7C)cycloalkyl(1–6C)alkyl, aryl, aryl(1–6C)allyl, heteroaryl, heteroaryl(1–6C)alkyl and $CH_2Y$ in which Y is $(CHOH)_nCH_2OH$ or $(CH_2)_nR^c$ (wherein n is an integer from 1 to 5) and in which $R^a$ and $R_b$ (except when $CH_2Y$) independently may bear a $COR^c$ substituent; or $NR^aR^b$ forms a pyrrolyl, pyrrolinyl, pyrrolidinyl, piperidino, piperazinyl, morpholino, thiomorpholino (or S-oxide) or perhydroazepinyl ring which may further bear one or more (1–6C)alkyl, phenyl, phenyl(1–4C)alkyl, phenoxy or phenyl(1–4C)alkyl substituents;

$R^4$ is (2–6C)alkenyl, (2–6C)alkynyl, aryl or heteroaryl and $R^4$ independently may bear $COR^c$; —OH or —O(1–4C)alkyl; (1–4C)alkyl, -(1–4C)alkylcarboxy (1–4C)alkyl, aryl or —Si— and wherein $R^c$ is hydroxy, (1–4C)alkoxy, or $NR^dR^e$ in which $R^d$ and $R^e$ are independently selected from hydrogen, (1–3C) alkyl, benzyl or phenyl wherein the aryl portion may be unsubstituted or substituted with halogen, (1–4C)alkyl or (1–5C)O—; or $NR^dR^e$ forms a pyrrolyl, pyrrolinyl, pyrrolidinyl, piperidino, piperazinyl (which may bear a (1–3C)alkyl or benzyl substituent at the 4-position), morpholino, thiomorpholino (or S-oxide) or perhydroazepinyl ring;

and wherein each aryl moiety is selected from a phenyl radical or an ortho-fused bicyclic carbocyclic radical having nine to ten ring atoms in which at least one ring is aromatic; and each heteroaryl moiety is a radical attached via a ring carbon of a monocyclic aromatic ring containing five ring atoms consisting of carbon and one to four heteroatoms selected from oxygen, sulfur and nitrogen, or containing six ring atoms consisting of carbon and one or two nitrogens;

and in which an aryl or heteroaryl portion of $R^3$ or $R^4$ may bear one or more halo, trifluoromethyl, (1–6C)alkyl, (2–6C)alkenyl, phenyl, phenyl(1–4C)alkyl, hydroxy, (1–6C)alkoxy, phenoxy, phenyl(1–4C)alkoxy, nitro, amino, (1–4C)acylamino, trifluoroacetylamino, carboxy, (1–3C)alkoxy-carbonyl or a phenyl carbonyl group; a 1,3 dioxolo group; a -(1–4C)alkylNRR' wherein R or R' is H or (1–4C)alkyl; a -(1–4C)alkylCN or cyano substituents;

or a pharmaceutically acceptable salt thereof;

comprising the steps of:

(a) reacting a corresponding compound of formula II

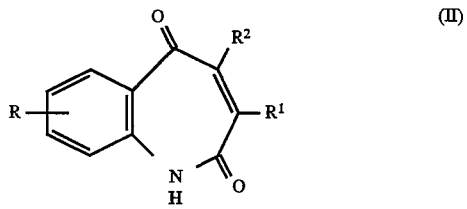

in which $R^1$ is alkoxy and $R^2$ is bromo or iodo with a tin reagent selected from $R^4SnL_3$ or $(R^4)_4Sn$ wherein L is selected from (1–6C)alkyl in the present of a palladium catalyst chosen from Pd(II) or Pd(O) in an inert hydrocarbon solvent or equivalent solvent at a temperature from ambient to reflux temperature or, if the compound of formula I produced in steps (a) and (b) above is a 4-alkenoic acid derivative, the corresponding alkoxy carbonyl species within formula I is added to a suitable solvent such as methylene chloride or equivalent solvent and treated with an acid or, if the compound of formula I is a 3-hydroxy species, the corresponding 3-alkoxy derivative is hydrolyzed in aqueous sodium bicarbonate or other base or, if the compound of formula I is a 3-hydroxy-4-alkoxycarbonylalkenyl, alkynyl or aryl species produced in steps (a) and (b) above or a carbamoyl compound, the corresponding 3-methoxy species is treated with lithium hydroxide monohydrate in a suitable solvent such as THF or its equivalent or, if the compound of formula I is an acrylamide species, a 3-alkoxy-4-alkenoic or 4-alkynoic compound within formula I produced via steps (a) and Co) is treated with an amine selected from $NR^1R^2$ wherein $R^1$ and $R^2$ is H, alkyl or aryl in a suitable solvent selected from DMF or its equivalent and an HCl scavenger.

* * * * *

UNITED STATES PATENT AND TRADEMARK OFFICE
CERTIFICATE OF CORRECTION

PATENT NO. : 5,656,626
DATED : AUGUST 12, 1997
INVENTOR(S) : MARC J. CHAPDELAINE ET AL.

It is certified that error appears in the above-identified patent and that said Letters Patent is hereby corrected as shown below:

Column 33, Claim 5, line 51, delete the space before "-methoxy-4-(2-thienyl)-1H-benzo(b)azepine-".

Column 35, Claim 7, line 14 "drag" should read as -- drug --.

Column 35, Claim 11, line 54, "aryl(1-6C)allyl," should read as -- aryl(1-6C)alkyl, --.

Column 36, Claim 11, line 62, "Co)" should read as -- (b) --.

Signed and Sealed this

Thirtieth Day of December, 1997

Attest:

BRUCE LEHMAN

Attesting Officer

Commissioner of Patents and Trademarks